United States Patent [19]
Sessler et al.

[11] Patent Number: 5,587,478
[45] Date of Patent: Dec. 24, 1996

[54] SAPPHYRIN MULTIMERS

[75] Inventors: Jonathan L. Sessler; Vladimir Král; Andrei Andrievsky, all of Austin, Tex.

[73] Assignee: Board of Regents, The University of Texas System, Austin, Tex.

[21] Appl. No.: 405,275

[22] Filed: Mar. 15, 1995

Related U.S. Application Data

[63] Continuation-in-part of Ser. No. 964,607, Oct. 21, 1992, Pat. No. 5,457,195.

[51] Int. Cl.$^6$ .......................... C07D 487/22; C08G 10/02
[52] U.S. Cl. .......................... 540/474; 540/472; 540/145; 536/28.1; 536/28.2; 528/230
[58] Field of Search .......................... 528/230; 540/145, 540/472, 474; 536/28.1

[56] References Cited

U.S. PATENT DOCUMENTS

| | | | |
|---|---|---|---|
| 4,318,825 | 3/1982 | Frame | 252/428 |
| 4,835,263 | 5/1989 | Nguyen et al. | 536/27 |
| 4,878,891 | 11/1989 | Millard | 604/5 |
| 4,883,790 | 11/1989 | Levy et al. | 540/145 |
| 4,915,683 | 4/1990 | Sieber | 604/4 |
| 4,935,498 | 6/1990 | Sessler et al. | 534/15 |
| 5,041,078 | 8/1991 | Matthews et al. | 604/4 |
| 5,120,411 | 6/1992 | Sessler et al. | 204/157.15 |
| 5,141,911 | 8/1992 | Meunier et al. | 502/159 |
| 5,159,065 | 10/1992 | Sessler et al. | 534/15 |
| 5,162,509 | 11/1992 | Sessler et al. | 534/15 |
| 5,190,966 | 3/1993 | Dougherty et al. | 514/410 |
| 5,242,797 | 9/1993 | Hirschfeld | 435/6 |
| 5,252,698 | 10/1993 | Bhardwaj et al. | 528/230 |
| 5,252,720 | 10/1993 | Sessler et al. | 534/11 |
| 5,272,056 | 12/1993 | Burrows et al. | 435/6 |
| 5,302,714 | 4/1994 | Sessler et al. | 540/472 |
| 5,371,199 | 12/1994 | Therien et al. | 540/145 |

FOREIGN PATENT DOCUMENTS

| | | |
|---|---|---|
| 0111418 | 6/1984 | European Pat. Off. . |
| 0196515 | 3/1986 | European Pat. Off. . |
| 0233701 | 1/1987 | European Pat. Off. . |
| WO90/10633 | 9/1990 | WIPO . |
| WO94/09003 | 4/1994 | WIPO . |

OTHER PUBLICATIONS

Aoyama et al., "Multi-Point Interaction of Phosphates with Protonated Pyridylporphyrin. Discrimination of Monoalkyl and Dialkyl Phosphates," *Chemistry Letters*, 1241–1244 (1991).

Bauer et al., "Sapphyrins: Novel Aromatic Pentapyrrolic Macrocycles," *J Am Chem Soc*, 105:6429–6436 (1983).

Broadhurst and Grigg, "18- and 22-π-Electron Macrocycles Containing Furan, Pyrrole, and Thiophen," *Chemical Communications*, 1480–1482 (1969).

Broadhurst and Grigg, "The Synthesis of 22 π-Electron Macrocycles. Sapphyrins and Related Compounds," *JCS Perkin*, 2111–2116 (1972).

Claude et al., "Binding of Nucleosides, Nucleotides, and Anionic Planar Substrates by Bis-Intercaland Receptor Molecules," *J Chem Soc, Chem Commun*, 17:1182–1185 (1991).

Cramer et al., "Synthesis and Structure of the Chloride and Nitrate Inclusion Complexes of [16-Pyrimidinium crown-4]," *J Am Chem Soc*, 113:7033–7034 (1991).

Cuellar and Marks, "Synthesis and Characterization of Metallo and Metal–Free Octaalkylphthalocyanines and Uranyl Decaalkylsuperphthalocyanines," *Inorg Chem*, 20:3766–3770 (1981).

Dietrich et al., "Proton Coupled Membrane Transport of Anions Mediated by Cryptate Carriers," *J Chem Soc Chem Comm*, 11:691–692 (1988).

Dixon et al., "Molecular Recognition: Bis–Acylguanidiniums Provide a Simple Family of Receptors for Phosphodiesters," *J Am Chem Soc*, 114:365–366 (1992).

Furuta et al., "Phosphate Anion Binding: Enhanced Transport of Nucleotide Monophosphates Using a Sapphyrin Carrier," *J Am Chem Soc*, 113:6677–6678 (1991).

Furuta et al., "Enhanced Transport of Nucleosides and Nucleoside Analogues with Complementary Base–Pairing Agents," *J Am Chem Soc*, 113:4706–4707 (1991).

Galan et al., "A Synthetic Receptor for Dinucleotides," *J Am Chem Soc*, 113:9424–9425 (1991).

Galan et al., "Selective Complexation of Adenosine Monophosphate Nucleotides by Rigid Bicyclic Guanidinium Abiotic Receptors," *Tetrahedron Letters*, 32(15):1827–1830 (1991).

Harriman et al., "Metallotexaphyrins: A New Family of Photosensitisers for Efficient Generation of Singlet Oxygen," *J Chem Soc Chem Comm*, 314–316 (1989).

Hisatome et al., "Porphyrins Coupled with Nucleoside Bases. Synthesis and Characterization of Adenine– and Thymine–Porphyrin Derivatives," *Chem Lett*, 2251–2254 (1990).

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J Am Chem Soc*, 112:3896–3904 (1990).

Hosseini et al., "Multiple Molecular Recognition and Catalysis. Nucleotide Binding and ATP Hydrolysis by a Receptor Molecule Bearing an Anion Binding Site, an Intercalator Group and a Catalytic Site," *J Chem Soc Chem Comm*, 9:596–598 (1988).

Kimura et al., "A Study of New Bis(macrocyclic polyamine) Ligands as Inorganic and Organic Anion Receptors," *J Org Chem*, 55(1):46–48 (1990).

(List continued on next page.)

*Primary Examiner*—Mukund J. Shah
*Assistant Examiner*—Pavanaram K. Sripada
*Attorney, Agent, or Firm*—Arnold, White & Durkee

[57] ABSTRACT

The present invention provides novel sapphyrin dimers, trimers, oligomers and polymers, which multimers may include repeating units of sapphyrin or sapphyrin derivatives alone, or may further incorporate other units such as nucleobases.

20 Claims, 1 Drawing Sheet

OTHER PUBLICATIONS

Kimura, "Macrocyclic Polyamines as Biological Cation and Anion Complexones—An Application to Calculi Dissolution," 113–141.

Kral et al., "Synthetic Sapphyrin–Cytosine Conjugates: Carriers for Selective Nucleotide Transport at Neutral pH," *J Am Chem Soc;* 114:8704–8705 (1992).

Li and Diederich, "Carriers for Liquid Membrane Transport of Nucleotide 5'–Triphosphates," *J Org Chem,* 47:3449–3454 (1992).

Marks and Stojakowvic, "Large Metal Ion–Centered Template Reactions. Chemical and Spectral Studies of the 'Superphthalocyanine' Dioxocyclopentakis (1–iminoisoindolinato)uranium(VI) and Its Derivatives," *J Am Chem Soc,* 1695–1705 (1978).

Rexhausen and Gossauer, "The Synthesis of a New 22 π–Electron Macrocycle: Pentaphyrin," *Chem Soc Chem Comm,* 6:275 (1983).

Schmidtchen, "A Non–Macrocyclic Host for Binding Organic Phosphates in Protic Solvents," *Tetr Lett,* 30(34):4493–4496 (1989).

Seel and Vogtle, "Molecular Recognition and Transport of Nucleobases—Superiority of Macrobicyclid Host Molecules," *Angew Chem Int Ed Engl,* 30(4):442–444 (1991).

Sessler et al., "Anion Binding: A New Direction in Porphyrin–Related Research," *Pure & Appl Chem,* 65(3):393–398 (1993).

Sessler et al., "Cytosine Amine Derivatives," *J Org Chem,* 47:826–834 (1992).

Sessler et al., "Enhanced Transport of Fluoride Anion Effected Using Protonated Sapphyrin as a Carrier," *J Chem Soc Chem Comm,* 1732–1735 (1991).

Sessler et al., "In vitro photodynamic activity of diprotonated sapphyrin: a 22–π–electron pentapyrrolic porphyrin–like macrocycle," *Chem Abstr,* 112:348–349, 112:194584t (1990).

Sessler et al., "A water–stable gadolinium (III) complex derived from a new pentadentate expanded porphyrin ligand," *Chem Abstr,* 111:720, 111:125716e (1989).

Sessler et al., "Synthetic and Structural Studies of Sapphyrin, a 22–π–Electron Pentapyrrolic 'Expanded Porphyrin'," *J Am Chem Soc,* 112:2810–2813 (1990).

Sessler et al., "An 'Expanded Porphyrin': The Synthesis and Structure of a New Aromatic Pentadentate Ligand," *J Am Chem Soc,* 110:5586–5588 (1988).

Shionoya et al., "Diprotonated Sapphyrin: A Fluoride Selective Halide Anion Receptor," *J Am Chem Soc,* 114:5714–5722 (1992).

Tabushi et al., "Lipophilic Diammonium Cation Having a Rigid Structure Complementary to Pyrophosphate Dianions of Nucleotides. Selective Extraction and Transport of Nucleotides," *J Am Chem Soc,* 103:6152–6157 (1981).

Tohda et al., "Liquid Membrane Electrode for Guanosine Nucleotides Using a Cytosine–Pendant Triamine Host as the Sensory Element," *Analyt Chem,* 64(8):960–964 (1992).

International Search Report, mailed Feb. 3, 1994.

International Search Report, mailed Feb. 22, 1994.

Iverson et al., "Phosphate Recognition by Sapphyrin. A New Approach to DNA Binding," *J. Am. Chem. Soc.,* 115:11022–11023, 1993.

Sessler et al., "Phosphate Anion Chelation and Base-pairing. Design of Receptors and Carriers for Nucleotides and Nucleotide Analogs," *Supramolec. Chem.,* 1:209–220, 1993.

Sessler et al., "Expanded Porphyrins. Receptors for Cationic, Anionic, and Neutral Substrates," in *Transition Metals in Supramolecular Chemistry,* NATO ASI Series; Fabbrizzi, L. and Poggi, A., Eds., Kluwer, Dorderecht, Series C, 448:391–408, 1994.

Gossauer, Albert, "Syntheses of Some Unusual Polypyrrole Macrocycles," *Bull. Soc. Chim. Belg.,* 92(9):793–795, 1983.

Král et al., "A Covalently Linked Sapphyrin Dimer. A New Receptor for Dicarboxylate Anions," *J. Am. Chem. Soc.,* 117:2953–2954, 1995.

Kus et al., "First Representatives of Porphyrinylnucleosides," name of publication unknown, 5133–5134 (1990).

Collman et al., "Synthesis of 'Face to Face' Porphyrin Dimers Linked by 5, 15–Substituents: Potential Binuclear Multielectron Redox Catalysts," *JACS,* 103:516–533 (1981).

Franck et al., "Synthese von Geschütztem Nor– und Homoporphobilinogen," *Liebigs Ann. Chem.,* 253–262 (1980).

Grigg et al., "Studies in Furan Chemistry. Part IV[1] 2,2'–Bifurans," *J. Chem. Soc.,* C:976–981 (1966).

Kambe and Yasuda, "The Potassium Flouride–Catalyzed Reaction. V. Aldol Condensation of Nitroalkanes and Aliphatic Aledhydes," *Bull. Chem. Soc. of Japan,* 41(6):1444–1446 (1968).

Tindall, "Esters of Nitroalcohols," *Industrial and Engineering Chemistry,* 33(1):65–66 (1941).

PCT Search Report for PCT/US90/01208, mailed Aug. 2, 1990, printed in USA.

International Search Report for International Application No. PCT/US90/07609, published in Europe.

Barton and Zard, "A New Synthesis of Pyrroles from Nitroalkenes," *J. Chem. Soc., Chem. Commun.,* pp. 1098–1100 (1985).

Broadhurst et al., "New Macrocyclic Aromatic Systems Related to Porphins," *Chem. Commun.,* pp. 23–24 (1969).

Broadhurst et al., "Preparation of Some Sulphur–containing Polypyrrolic Macrocyles. Sulphur Extrusion from a meso–Thiaphlorin," *Chem. Commun.,* pp. 807–809 (1970).

Maiya et al., "In Vitro Photodynamic Activity of Diprotonated Sapphyrin: a 22–pi–electron Pentapyrrolic Porphyrin–like Macrocycle," *Chem. Absts.,* 112:348–349, Abstract #194584t (1990).

Sessler et al., "Synthesis and Crystal Structure of a Novel Tripyrrane–Containing Porphyrinogen–like Macrocycle," *J. Org. Chem.,* 52:4394–4397 (1987).

Franck et al., "Einfache Biomimetische Porphyrin–Synthesen," *Liebigs Ann. Chem.,* 263–274 (1980).

Wardle, "The surface of malignant and virus transformed cells," *Cell Surface Science in Medicine and Pathology,* Elsevier Science Publishing Co, Inc., New York, Ch. 19, pp. 552–561, (1985).

Verlhac & Gaudemer, "Water–soluble porphyrins and metalloporphyrins as photosensitizers in aerated aqueous solutions. I. Detection and determination of quantum yield of formation of singlet oxygen," *Nouveau Journal De Chimie,* 8:401–406, (1984).

Král & Sessler, "Molecular Recognition via Base–pairing and Phosphate Chelation. Ditopic and Tritopic Sapphyrin–based Receoptors for the Recognition and Transport of Nucleotide Monophosphates," *Tetrahedron,* 51(2):539–554, (1995).

Whitfield et al., "Differential reactivity of carbohydrate hytdroxyls in glycosylations. II. The likely role of intramolecular hydrogen bonding on glycosylation reactions. Galactosylation of nucleoside 5'-dydroxyls for the syntheses of novel potential anticancer agents," *Can. J. Chem.*, 72:2225–2238, (1994).

Schmidt, "Anomeric–oxygen activation for glycoside synthesis: the trichloroacetimidate method," *Advance in Carbohydrate Chemistry and Biochemistry*, 50:21–123, (1994).

Sessler et al., "Sapphyrins: New Life for an Old 'Expanded Porphyrin'", *Synlet*, Mar., 127–134, (1991).

SAPPHYRIN MULTIMERS

The government owns rights in the present invention pursuant to NIH grants AI 28845 and AI 33577.

This application is a continuation-in-part application of U.S. Ser. No. 07/964,607, filed Oct. 21, 1992, now U.S. Pat. No. 5,457,195, which reference is incorporated by reference herein.

BACKGROUND OF THE INVENTION

1. Field of the Invention

The present invention relates generally to sapphyrin multimers, and derivatives and conjugates thereof. The multimers include dimers, trimers, oligomers and polymers of sapphyrin or sapphyrin derivatives, either alone, or in combination with other units such as nucleobases.

2. Description of the Related Art

Sapphyrins are large pyrrole-containing macrocyclic analogues of the porphyrins. A number of expanded porphyrin systems are now known. However, only a few fully conjugated examples have been reported that contain more than four pyrrolic subunits, namely the smaragdyrins, sapphyrins, pentaphyrins, hexaphyrins, and superphthalocyanines[1] (Sessler & Burrel, 1991).

Sapphyrin, first discovered serendipitously by Woodward[2] is one of the more intriguing products to emerge from initial studies directed towards the synthesis of Vitamin $B_{12}$.[2,3] It is a 22 pi-electron pentapyrrolic macrocycle which exhibits an intense Soret-like band at about 450 nm ($CHCl_3$) along with weaker Q-type transitions in the 620 to 690 nm region. These optical properties, along with the presence of a large central cavity which serves for metal binding, renders sapphyrin useful for certain biomedical applications, including photodynamic therapy (PDT) and magnetic resonance imaging enhancement (MRI).

In addition to the above, certain expanded porphyrins, including especially those of the sapphyrin series, have been found to act as halide anion chelating agents in both solution and the solid state[4]. This finding, along with an appreciation that the diprotonated form of 3,8,12,13,17,22-hexaethyl-2,7,18,23-tetramethylsapphyrin acts as an efficient carrier for the through-dichloromethane-membrane transport of nucleotide monophosphates, such as e.g. guanosine-5' monophosphate, and related entities at acidic pH[5] led the inventors to consider that the basic sapphyrin structure and related compounds such as the rubyrins, if suitably modified, could be used to bind, recognize, and transport phosphorylated entities at or near neutral pH.

Unfortunately, all sapphyrins known at the time of this invention were known both to be essentially insoluble in water and also known to be ineffective as through membrane carriers for phosphate monoesters including those specifically that define the class of compounds known as nucleotides and nucleotide analogues[5]. In addition, the sapphyrins known prior to the present invention were all of such simple character in terms of peripheral substituents, such that only hydrogen or alkyl were known[2,3]. These deficiencies limited the potential utility of sapphyrins for any applications associated with their use at or near neutral pH and, more generally, any conditions involving partial or complete association with an aqueous environment.

At present, no general set of nucleotide transport agents exists[10]. In early work Tabushi was able to effect adenosine nucleotide transport using a lipophilic, diazabicyclooctane-derived, quaternary amine system[10a]. However, this same system failed to mediate the transport of guanosine 5'-monophosphate (GMP) or other guanosine-derived nucleotides. Since then, considerable effort has been devoted to the generalized problem of nucleic acid base ("nucleobase") recognition, and various binding systems have been reported.

Currently known nucleotide binding systems include various acyclic, macrocyclic, and macrobicyclic polyaza systems[10a-10n]; nucleotide-binding bis-intercalands[10k]; guanidinium-based receptors[10f,10n]; and various rationally designed H-bonding receptors[10o-10u]. These latter H-bonding receptors have been shown to be effective for the chelation of neutral nucleobase and/or nucleoside derived substrates but, without exception, have all proved unsatisfactory for the important task of charged nucleotide recognition. Thus, despite intensive efforts in this field, there is currently no synthetic system capable of effecting the recognition, or through-membrane transport, of phosphate-bearing species such as anti-viral compounds. Furthermore, there are presently no rationally designed receptors which are "tunable" for the selective complexation of a given nucleobase-derived system.

Not surprisingly, the transport of larger polyphosphorylated compounds across cellular membranes also poses significant problems. The difficulties in transporting oligonucleotides across the plasma membrane and into mammalian cells is one of the factors currently limiting the successful application of antisense technology to human therapy. Further limitations may also result from the dynamics of oligonucleotide recognition, binding and functional inhibition which occurs intracellularly, subsequent to any import that does occur.

There is clearly, therefore, a major need for novel drug delivery systems to be developed. Compounds which would allow negatively-charged (anionic) structures, particularly phosphate-bearing compounds, including nucleotides and nucleotide derivatives such as anti-viral compounds and anti-sense oligonucleotides, to be transported across naturally lipophilic cellular membranes would represent an important scientific and medical advance.

In addition to the delivery of compounds to cells, there still remains considerable scope for the design of improved chemotherapeutic compounds which act upon DNA once inside a target cell. Since currently available chemotherapeutic agents have complex structures, or complicated modes of interaction with their targets that preclude systematic improvement, the development of a novel class of DNA binding compounds would open up new avenues for the design of improved therapeutics. In this regard, a class of compounds that can be modified in a number of different ways while maintaining their overall oligomeric, or polymeric structure would be particularly advantageous. The same is true for compounds that can be activated by light, or other means, to produce singlet oxygen or hydroxyl radicals, once bound to DNA. These considerations provided the present inventors with further impetus for the design and synthesis of improved sapphyrins such as those embodied by the present invention.

SUMMARY OF THE INVENTION

The present invention addresses these and other shortcomings in the prior art through the synthesis of several multimers of sapphyrin or sapphyrin derivatives. In a general and overall sense, included within the novel compounds of the invention are sapphyrin dimers, trimers, oligomers and polymers. Multimers will typically comprise sapphyrin or sapphyrin derivatives alone, or sapphyrin in combination with other units such as nucleobases, as well as complexes of sapphyrin-nucleobase polymers with oligonucleotides, for example.

In general terms, sapphyrin multimers of the present invention can be defined by the following general structure:

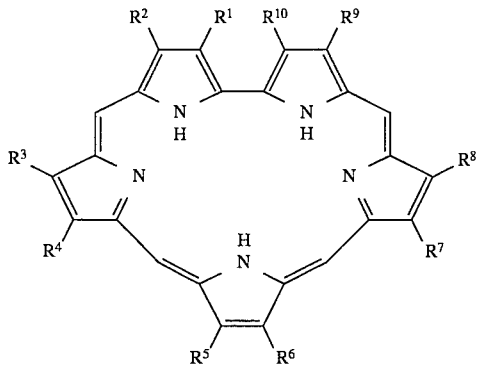

wherein each of $R^1$–$R^{10}$ are independently hydrogen, alkyl, alkene, alkyne, halide, alkylhalide, hydroxyalkyl, hydroxyalkylamido, glycol, polyglycol, thiol, thioalkyl, aminoalkyl, carboxyalkyl, carboxyamidealkyl, oxyalkyl, alkoxyalkyl, aryloxyalkyl, oxyhydroxyalkyl, alkyloxycarbonyl, aryloxycarbonyl, aldehyde, ether, ketone, carboxylic acid, phosphate, phosphonate, saccharide, nucleobase, sulfate, phosphate substituted alkyl, phosphonate substituted alkyl or sulfate substituted alkyl, such that the total number of carbon atoms in each substituent R is less than or equal to 10,000.

as used herein refers to any derivative or conjugate of sapphyrin including, but not limited to, alkyl and carboxyalkyl sapphyrins, water-soluble sapphyrins such as sapphyrin-sugar compounds and polyhydroxysapphyrins, sapphyrin-metal chelator conjugates, and sapphyrin-nucleobase conjugates.

The B substituent can include any sapphyrin, sapphyrin derivative, polysapphyrin, or oligosapphyrin. Conjugation of further derivatives to form a sapphyrin oligomer or polymer may be via any of the R groups $R^1$–$R^{10}$, with $R^4$, $R^5$ and $R^7$ being preferred targets. Conjugation at more than one point is also contemplated and may be via any two, or more, of the R groups $R^1$–$R^{10}$, such as $R^4$ and $R^7$, $R^3$ and $R^8$, or $R^5$ and $R^6$, for example As used herein, the terms "sapphyrin multimer" and "multimer of sapphyrin" are intended to refer to any compound which includes at least two sapphyrin macrocycles joined covalently by a linking group. Moreover, the term "sapphyrin oligomer" or "oligosapphyrin" is intended to refer to sapphyrin-containing structures having a more defined length, such as from 2 or 3 up to 20 or so sapphyrin units/molecule and the term "sapphyrin polymer" or "polysapphyrin" is intended to refer to sapphyrin-containing structures having up to about 200 sapphyrin units/molecule. Preferably, a sapphyrin polymer has about 30–60 sapphyrin units.

Structure II represents the general structure for the dimeric sapphyrins of this invention, and is an example of structure I, wherein a further sapphyrin derivative has been added. Structure II includes $R^1$–$R^{18}$ each R group may be independently any of the groups listed above for $R^1$–$R^{10}$, and also "A", which is as herein defined.

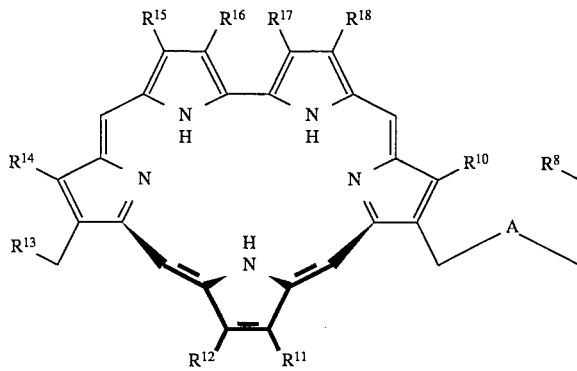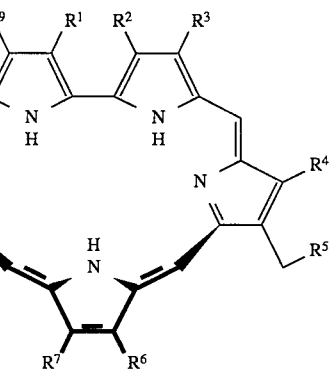

STRUCTURE II

In this general sapphyrin multimer structure, at least one of $R^1$–$R^{10}$ is of the formula $(CH_2)_n$—A—$(CH_2)_m$—B; where A is alkyl, oxy, sulfide, amide, carbonyl, alkenyl, alkynyl, aryl, alkylhalide, hydroxyalkyl, glycol, polyglycol, alkylthiol, substituted alkyl, phosphate, phosphonate, sulfate, phosphate substituted alkyl, phosphonate substituted alkyl, sulfate substituted alkyl, carbonate, carbamate, bis(aminoguanidinium), carboxy, carboxyamide, carboxyamidealkyl, carboxyamidearyl, thiol-substituted carboxyamide, or derivatized carboxyamide; and B is a sapphyrin or a sapphyrin derivative, or an oligomer or polymer of sapphyrin or of a sapphyrin derivative; and n and m are independently an integer from 0 to 10.

The novel aspect of the foregoing structure is the fact that in the context of the present invention, at least one R group substituent will be of the general formula X-B, wherein X is any sapphyrin compound and B is another sapphyrin or sapphyrin derivative, or is a polymer or oligomer of sapphyrin or of a sapphyrin derivative. "Sapphyrin derivative"

Structure III represents the general structure for the polymeric sapphyrins of the present invention. Structure III is a more specific polymeric example of both structures I and II, wherein further sapphyrin derivatives or other moieties, such as oligonucleotides or sapphyrin-oligonucleotides, have been added. In structure III, t may be from 1–100, or even from 1–200, and $R^1$–$R^{10}$ and A may be as defined herein.

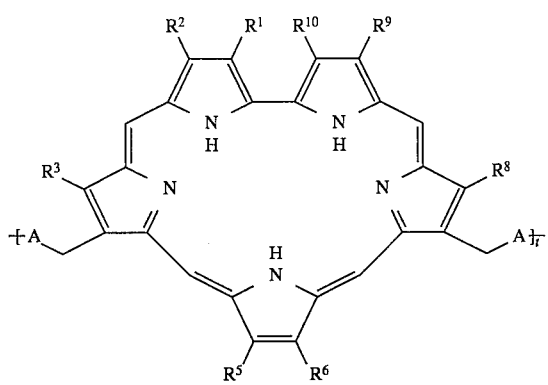

III

Preferred sapphyrin multimers are: i) wherein A is carboxyamidearyl or carboxyamidealkyl, B is a sapphyrin or a sapphyrin derivative, and n and m are independently 1, 2 or 3; ii) wherein B is a sapphyrin derivative and the sapphyrin derivative is hydroxyalkyl, saccharide or aminosaccharide derivative; iii) wherein A is carboxyamidealkyl bound to a further amide; and the further amide is covalently bound to two molecules of B to form a tethered sapphyrin trimer; iv) wherein B is sapphyrin or sapphyrin derivative and B is further bound to a third sapphyrin or sapphyrin derivative to form a linear sapphyrin trimer; v) wherein the abovenamed linear sapphyrin trimer is covalently bound to form a cyclic trimer; vi) wherein A is carboxyamidealkyl bound to a further amide; the further amide being covalently bound to a second sapphyrin and a linker, the linker being bound to a third and a fourth sapphyrin to form a tethered sapphyrin tetramer; vii) the abovenamed tetramer where the linker is a tertiary amine; viii) wherein B is an oligomer or polymer of sapphyrin or sapphyrin derivative; ix) wherein B is a polymer of sapphyrin or sapphyrin derivative having from 4 to about 200 sapphyrin units; x) wherein A is phosphate; xi) wherein at least one of $R^1$–$R^{10}$ is a nucleobase; xii) where B is a sapphyrin derivative and the derivative is a nucleobase; xiii) wherein B is a polymer of sapphyrin derivative and the derivative is a nucleobase; or xiv) a sapphyrin multimer further comprising a noncovalently bound oligonucleotide.

Particularly preferred sapphyrin multimers are those of structure 14, 15, 15b, 15c, 19, 21, 22, 23, 24, 25, 26, 27, 34, 35, or 36.

A further embodiment of the present invention is a method of making a sapphyrin multimer comprising the steps of i) obtaining a sapphyrin or sapphyrin derivative, and ii) reacting the sapphyrin or sapphyrin derivative with a further sapphyrin or sapphyrin derivative to form a sapphyrin multimer. Preferred multimers are dimers; a tethered, linear, or cyclic trimer; a tethered tetramer; an oligomer of about 2–20 sapphyrin units, or a polymer of about 3 to 200 sapphyrin units, preferably about 30–60 sapphyrin units.

It is contemplated that stepwise synthesis of sapphyrin-multimer-oligonucleotide conjugates may be performed manually or may be automated, and may be in a solution-phase or on a solid support. Solid support synthesis may be accomplished using an automated or a manual nucleic acid synthesizer. Common solid supports are CPG (control pore glass) and CPS (control pore silica). Other possible solid supports include polystyrene, polyamide/Kieselguhr, and cellulose paper. A preferred embodiment of this method is automated synthesis on a solid support. Attachment of a sapphyrin multimer to an oligonucleotide during stepwise synthesis obviates the need for a postmodification protocol and a second purification of the product. This results in an improved yield and greatly facilitates scale-up.

Another aspect of the present invention is a method of binding an anion comprising the step of contacting the anion with a multimeric sapphyrin or sapphyrin derivative. The anion is preferably a phosphate or dicarboxylate anion. Protonated sapphyrin dimers are demonstrated herein to act as effective receptors for certain dicarboxylate anions. The sapphyrin molecule itself remains monoprotonated in the pH range of about 3.5–10. A high selectivity was demonstrated for benzene dicarboxylate anions, especially the para isomer. One skilled in the art in light of this disclosure would realize that multiple molecules of dicarboxylate anion may be bound by a sapphyrin multimer. A variety of physiologically important dianion species may, therefore, be bound and detected and/or transported by sapphyrin multimers, including fatty acids, and phosphates, for example.

A further aspect of the present invention is a method of transporting an anion from a source to a receiving phase, the method comprising the steps of: i) obtaining an anion in a source; and ii) contacting the anion with a protonated multimer of sapphyrin or sapphyrin derivative as described herein above, wherein the multimer releases the anion to the receiving phase. The anion is preferably a dicarboxylate anion, and more preferably, a benzene dicarboxylate anion, and even more preferably, a para isomer of a benzene dicarboxylate anion.

It will be appreciated by those of skill in the art that the invention is also generally applicable to the introduction of a sapphyrin multimer, alone or complexed with a second molecule, into an organism or, more generally, a cell contained within an organism. This may be employed as a means, for example, of successfully introducing the second compound (typically a charged compound) into the cell. An example might be introduction of a complex which includes an antimetabolic or antienzymatic compound such as an antiviral antimetabolic or antienzymatic compound, which one desires to introduce into a virally infected target cell. Another example would be the introduction of an antimetabolic or antienzymatic antitumor or antiproliferative compound that is introduced into a targeted tumor or proliferating cell. Of course, it is contemplated that the target cell may be located within an animal or human patient, in which case the complex is administered in effective amounts in an effective manner to the patient.

Generally speaking, it is contemplated by the inventors that useful pharmaceutical compositions of the present invention will include the selected sapphyrin multimer (which preferably incorporates a water-soluble sapphyrin macrocycle) in a therapeutically effective amount that is diluted in a physiological buffer, such as phosphate buffered saline. The route of administration and ultimate amount of material that is administered to the patient or animal under such circumstances will depend upon the intended application and will be apparent to those of skill in the art in light of the examples which follow. Preferred routes of administration will typically include parenteral or topical routes.

DETAILED DESCRIPTION OF THE PREFERRED EMBODIMENTS

Figure 1:
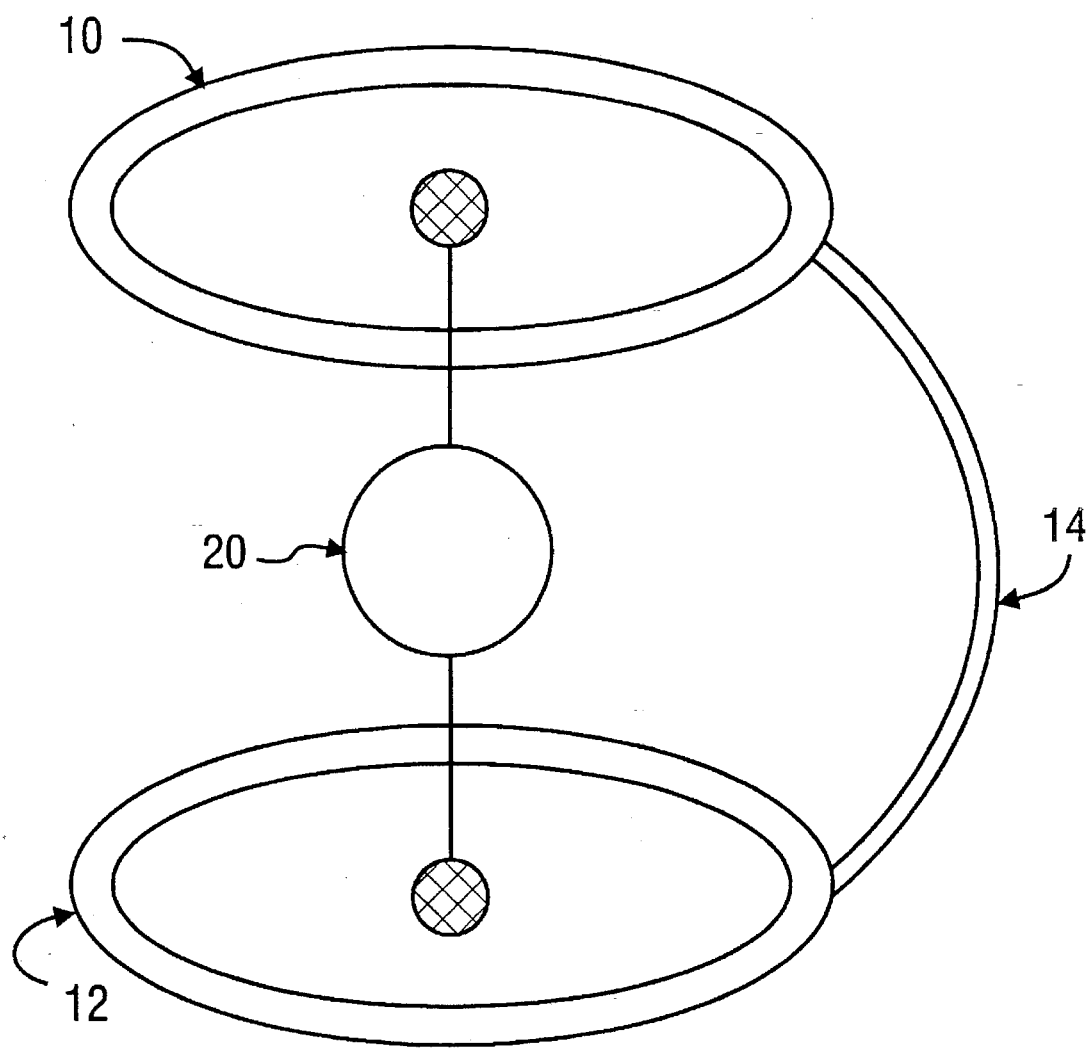
FIG. 1 provides a schematic representation of the proposed supramolecular complex formed between a sapphyrin dimer and a dicarboxylate substrate.

The synthesis of various sapphyrins has been previously reported[2-6,11,12], see also, U.S. Pat. Nos. 5,159,065, 5,120, 411, 5,041,078, 5,302,714, and U.S. Ser. No. 07/964,607;

each of these references is incorporated herein by reference. The present invention concerns a variety of new sapphyrin-based systems, in which the sapphyrin molecule has been "multimerized" in a number of novel ways. In particular, this invention encompasses dimeric, trimeric, oligomeric and polymeric sapphyrin multimers. Such sapphyrin multimers may comprise water-soluble sapphyrins, sapphyrin-metal chelator conjugates or sapphyrin-nucleobase conjugates.

These new sapphyrin species overcome known deficiencies associated with extant sapphyrins. This is because all sapphyrins known at the time of this invention were exclusively monomeric in nature and insoluble in aqueous media at or near neutral pH. Thus, the sapphyrins known prior to the present invention were incapable of forming well characterized, water-soluble complexes with phosphorylated entities, including DNA, RNA, nucleotides, nucleotide analogues, and simple phosphate and phosphonate monoesters, at or near neutral pH. Multimeric sapphyrins were unknown.

In addition, all sapphyrins known at the time of this invention were recognized to be quite limited in terms of their substitution patterns, bearing only alkyl groups in the so-called β-positions. Furthermore, this same lack of substituent versatility meant that sapphyrin systems carrying potentially reactive side chains were completely unknown and this too was recognized as limiting the utility of those few sapphyrins known to be extant at the time of this invention. Thus, the inventors felt it worthwhile to prepare oligomeric and polymeric sapphyrin systems, wherein the binding and recognition effects achieved in the monomeric sapphyrins might be expected to be greatly amplified.

Representative examples of alkanes useful as alkyl group substituents of sapphyrin oligomers or polymers include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by one or more functional groups as described herein.

Among the halide substituents, chloride, bromide, fluoride and iodide are contemplated in the practice of this invention. Representative examples of alkylhalides used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane; straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–3. A preferred oxyalkyl is $O(CH_2CH_2O)_x CH_3$ where $x=1–100$, preferably 1–10, and more preferably, 2–3.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate substituted alkyls include alkyls as described above substituted by one or more sulfate groups, a representative example of which is diethyl sulfate $((C_2H_5)_2SO_4)$.

Representative examples of phosphates include phosphate or polyphosphate groups. Representative examples of phosphate substituted alkyls include alkyls as described above substituted by one or more phosphate or polyphosphate groups. Representative examples of phosphonate substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary (CONHR') and tertiary (CONR'R") carboxyamides where each of R' and R" is a functional group as described herein.

Representative examples of useful amines include a primary, secondary or tertiary amine of an alkyl as described hereinabove. Hydroxyalkylamido refers to a substituent having a hydroxyalkyl and an amine group, the amine may be primary, secondary or tertiary.

"Hydroxyalkyl" means alkyl groups having hydroxyl groups attached. "Oxyalkyl" means alkyl groups attached to an oxygen. "Oxyhydroxyalkyl" means alkyl groups having ether or ester linkages, hydroxyl groups, substituted hydroxyl groups, carboxyl groups, substituted carboxyl groups or the like. "Saccharide" includes oxidized, reduced or substituted saccharide of Table 1, for example; saccharides such as in Table 1, derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. The saccharides employed may be either D or L forms and may also be either α or β forms. The use of modified saccharides is also envisioned, such as those including, for example, phosphate, methyl or amino groups. It is contemplated that preferred saccharides for use in accordance herewith will include, for example, glucose, glucosamine, galactose, galactosamine and mannose.

"Carboxyamidealkyl" means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

For the sapphyrins of the present invention, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$.

The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than ((2n+1)–q) q is zero or a positive integer less than or equal to 2n+1, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H alkyl, hydroxyalkyl, or $C_mH_{((2m+1)-r)}O_zR^b{}_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl, or $C_mH_{((2m+1)-r)}O_zR^b{}_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c{}_q$ or $OC_nH_{((2n+1)-q)}O_yR^c{}_q$ where n is a positive integer from 1 to 10; y is zero or a positive integer less than ((2n+1)–q), q is zero or a positive integer less than or equal to 2n+1, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl, or $C_mH_{((2m+1)-r)}O_zR^b{}_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

Certain particular embodiments of the invention relate to sapphyrin multimers comprising sapphyrin derivatives that are water-soluble due to the presence of hydroxy substituents on the sapphyrin periphery. Representative water-soluble sapphyrins are disclosed in parent application U.S. Ser. No. 07/964,607, incorporated herein by reference. Water-soluble sapphyrins are particularly desirable where one would like to exploit the various surprising properties of the sapphyrin macrocycle in connection with human or animal applications. The nature of the polyhydroxylation is not particularly critical to achieving water solubility of the sapphyrin multimer, so long as at least one, and preferably three or four hydroxyl groups per sapphyrin macrocycle are incorporated into the structure. The inventors have found that the introduction of at least one hydroxyl group per sapphyrin macrocycle will be sufficient to achieve some degree of water solubility.

One means for introducing hydroxyl groups into the sapphyrin macrocycle structure is simply through the addition of hydroxyalkyl substituents to the basic sapphyrin macrocycle unit, wherein the added substituents include one or more hydroxyl groups within their structures. Thus, exemplary polyhydroxylated sapphyrins will be those that are modified to include structures such as hydroxymethyl, hydroxyethyl, hydroxypropyl, hydroxybutyl, dihydroxyalkyl, trihydroxyalkyl, or the like, at one or more R positions of the basic sapphyrin structure shown above.

An alternative means of achieving polyhydroxylation is through the addition of sugar moieties such as a saccharide, polysaccharide, saccharide derivative or aminosaccharide, to the sapphyrin macrocycle structure. In such cases, it has been found that the addition of a single saccharide molecule to a sapphyrin macrocycle will achieve a degree of water solubility. These structures are referred to broadly herein as simply sapphyrin-sugar or sapphyrin-saccharide compounds, conjugates or derivatives. The nature of the sugar is not particular critical to the achievement of water solubility, and a non-exhaustive, exemplary list of useful sugars in this regard is set forth in Table 1.

TABLE 1

| Examples of Saccharides and Saccharide Derivatives | |
|---|---|
| Ribose | Fructose |
| Arabinose | Sorbose |
| Xylose | Tagatose |
| Lyxose | Fucose |
| Allose | |
| Altrose | Methylglucoside |
| Glucose | Glucose 6-phosphate |
| Mannose | |
| Gulose | N-Acetylgalactosamine |
| Idose | N-Acetylglucosamine |
| Galactose | Sialic Acid |
| Talose | Alginic Acid |
| Ribulose | Chitosan |
| Xylulose | Hyaluronic Acid |
| Psicose | |
| Sucrose | |
| Lactose | |
| Maltose | |

In still other embodiments, the present invention relates to sapphyrin multimers comprising sapphyrin-nucleobase conjugates. As used herein, the term "sapphyrin-nucleobase conjugate" is intended to refer broadly to any conjugate formed by the covalent conjugation of any sapphyrin macrocycle to any nucleobase. Moreover, as used herein the term "nucleobase" is intended to refer broadly to any moiety that includes within its structure a purine or pyrimidine, a nucleic acid, nucleoside, nucleotide, or any derivative of any of these. Thus, the term nucleobase includes adenine, cytosine, guanine, thymidine, uridine, inosine, or the like, bases, nucleotides or nucleosides, as well as any base, nucleotide or nucleoside derivative based upon these or related structures. Particular examples of a useful nucleobase are any purine or pyrimidine-based molecule that will effect an anticellular, antiviral, antitumor or antienzymatic effect, regardless of the underlying mechanism. Exemplary nucleobases are shown in Table 2, including preferred conjugates such as purine or pyrimidine antimetabolites such as FU, AraC, AZT, ddI, xyloGMP, Ara-AMP, PFA or LOMDP.

TABLE 2

| MODIFIED NUCLEOSIDE/NUCLEOTIDE ANALOGUE ANTI-METABOLITES |
|---|
| AraC |
| AraAMP |
| Azaribine |

TABLE 2-continued

MODIFIED NUCLEOSIDE/NUCLEOTIDE ANALOGUE ANTI-METABOLITES

Azathioprine
Azauridine
AZT
Bromodeoxyuridine
Chlorodeoxyuridine
Cytarabine
Deoxyuridine
DideoxyInosine DDI
Erythrohydroxynonyladenine
Floxuridine
Fluorouracil (5-FU)
Idoxuridine
LOMPD
Mercaptopurine
PFA
Thioguanine
Trifluoromethylde-oxyuridine
Xylo-GMP In still further embodiments, the nucleobase component of sapphyrin-nucleobase conjugates will include a protected nucleobase having attached substituents that protect the nucleobase from inappropriate or undesirable chemical reaction. Examples include substituents such as 9-fluorenylmethyl carbonyl, benzyloxycarbonyl, 4-methoxyphenacyloxycarbonyl, t-butyl oxycarbonyl, 1-adamantyloxycarbonyl, benzoyl, N-triphenylmethyl, N-di-(4-methoxyphenyl)phenylmethyl, and the like. Sapphyrin-nucleobase conjugates were demonstrated in the parent application Ser. No. 07/964,607 to effect the selective through-membrane transport of nucleoside monophosphates at, or near, neutral pH. It is contemplated that sapphyrin-nucleobase conjugates will have a wide variety of applications, ranging from their use as agents for selectively delivering an associated, biologically active nucleobase to a particular body or even subcellular locale. For example, in the case of antimetabolite nucleobases, it is contemplated that the sapphyrin-nucleobase conjugates will act to deliver the antimetabolite to subcellular sites through the DNA binding activity of the sapphyrin portion of the conjugate. Perhaps more importantly, it is recognized that many, many nucleobase antimetabolites cannot be readily employed in therapy due to the fact that their charged nature inhibits their uptake by target cells, or otherwise inhibits or suppresses their unencumbered movement across biological membranes. Typically, this shortcoming is due to the presence of charged structures such as phosphates, phosphonates, sulfates or sulfonates on the nucleobase which, due to their charged nature, prevents or inhibits their crossing of a biological membrane. It is proposed that sapphyrin multimers of the present invention can be employed as transport agents for carrying such nucleobases across membranes, (whether the nucleobase is directly conjugated to at least one of the sapphyrin macrocycles or simply complexed with it).

It is contemplated that multimers of sapphyrin-nucleobase conjugates can be employed to carry hydrogen bonded poly- or oligo-nucleotides into target cells through complementarity with the sequence of bases "encoded" on the sapphyrin-nucleobase polymer. One of the advantages of a sapphyrin multimer over a monomer is that a multimer will allow a more appropriate balance of charges between, for example, a polyanionic DNA and a polycationic sapphyrin.

The foregoing general structure could be exemplified by the formula:

wherein X is a sapphyrin macrocycle, N is a conjugated nucleobase structure, and Y is a hydrogen bonded poly- or oligonucleotide.

Alternatively, it is contemplated that sapphyrin multimers of the present invention may serve as a carrier for polymers of nucleobases, wherein the nucleobase polymers are attached covalently to the sapphyrin macrocycle, such as might be exemplified through the structural designation:

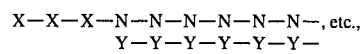

wherein X is a sapphyrin macrocycle, and N is a selected oligomeric or polymeric nucleotide or other nucleobase, and Y is a hydrogen bonded poly- or oligonucleotide. Such a structure would be useful in a number of contexts, such as a specific carrier for complementary nucleotides such as antisense molecules.

Due to the unique mode of DNA interaction, a sapphyrin polymeric molecule will possess an unrivaled ability to act as a general DNA binding platform. This has the distinct advantage that it can be modified so as to adjust both target cell specificity and degree of interaction with the DNA. For sapphyrin multimers, the basic site of interaction with the DNA involves the interior of the sapphyrin macrocycle, so that the exterior positions $R^1$–$R^{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrin multimers, including alkylating functions (bromoacetamido groups, epoxides etc.) to provide covalent attachment to DNA or ene-diyne moieties to allow for double-stranded cleavage.

A further and important advantage of the sapphyrin system is that the simple DNA binding motif has been extended to several multimeric structures, in which multiple sapphyrins covalently linked together will be able to bind simultaneously and thus strengthen the entire interaction. This feature will allow a modular approach in which the appropriate number (2-10, 2-15, 2-20, 2-25, 2-30 or 2-40) of sapphyrin molecules is attached in a single molecule, perhaps with different sapphyrin units containing sapphyrin derivatives with different groups attached that control such important properties as solubility, target cell specificity and DNA modification ability.

To synthesize multitopic receptors, the inventors developed strategies to address the following objectives: (i) the independent development of molecular recognition strategies for the complexation of two very different kinds of substrates (charged anionic and neutral nucleobase); (ii) their subsequent co-combination so as to provide receptors bearing both kinds of binding subunits; and (iii) various alternative methods of receptor oligomerization so as to provide oligomeric species bearing numerous combinations of multitopic receptors.

Pursuing these strategies led to the development of the sapphyrin-based ditopic receptor systems disclosed in parent application Ser. No. 07/964,607, capable of recognizing both the anionic phosphate and the neutral portions of the nucleotide derivatives, such as the purine or pyrimidine moieties. Molecules of this type are, indeed, capable of binding and transport of nucleotides and their derivatives. This theme was extended to the preparation of oligomeric, multitopic, receptors capable of recognizing multiple phosphate anions and nucleobase portions of nucleotide derivatives arranged in specific sequences.

The ditopic receptor systems are ideal vehicles for the intracellular transport of nucleotides and their derivatives, including anti-viral agents. The multitopic receptors, likewise are contemplated to be of use in binding to oligonucleotides and specific sections of DNA or RNA and in transporting such nucleic acid segments into cells. The phosphate and nucleic acid base ("nucleobase") recognition, through-membrane transport and cell delivery properties of the present invention are thus applicable to the recognition and delivery of a large variety of monomeric and oligomeric species, including DNA, RNA and antisense constructs.

The present invention therefore encompasses sapphyrin-nucleotide oligomers and polymers. The oligomeric linkage in such molecules may take place at various places in the sapphyrin or sapphyrin-nucleobase monomers.

The sapphyrin oligomers and polymers of the present invention include relatively low-number conjugates, such as dimers and trimers, and also larger oligomers or polymers. The oligomers will generally include between about 2 and about 8 residues, or even up to 20 residues, whereas the polymers may generally comprise up to about 100 residues, or even up to about 200 residues.

The monomeric units employed in the synthesis of sapphyrin multimers may be known sapphyrin molecules, such as those described in U.S. Pat. No. 5,159,065, incorporated herein by reference. Equally, any of the novel sapphyrin derivatives disclosed in parent application U.S. Ser. No. 07/964,607 may be employed, in any combination, to create further novel sapphyrin dimers, trimers, oligomers or polymers. Encompassed within the term "multimers" are those sapphyrin conjugates synthesized by the controlled addition of particular monomeric units and those produced by more uncontrolled polymerization methods.

The inventors have additionally found that sapphyrin dimers act as effective receptors for dicarboxylate anions. Di- and tricarboxylates are critical components of numerous metabolic processes including, for instance, the citric acid and glyoxylate cycles. They also play an important role in the generation of high energy phosphate bonds and in the biosynthesis of important intermediates. In the present invention, two protonated sapphyrins (10 and 12, FIG. 1) serve as the key carboxylate-binding "building blocks" to chelate a dicarboxylate anion (20) while a flexible diaminopropane "spacer" (14) serves as the macrocycle-to-macrocycle linking chain. This choice provides a system that rivals the best of the extant systems in terms of absolute binding efficacy in highly polar solvents (e.g., methanol) while displaying a very different kind of inherent substrate binding selectivity.

Sapphyrin Multimers

Specific examples of sapphyrin multimers include, but are not limited to, those compounds represented by structures 21–24.

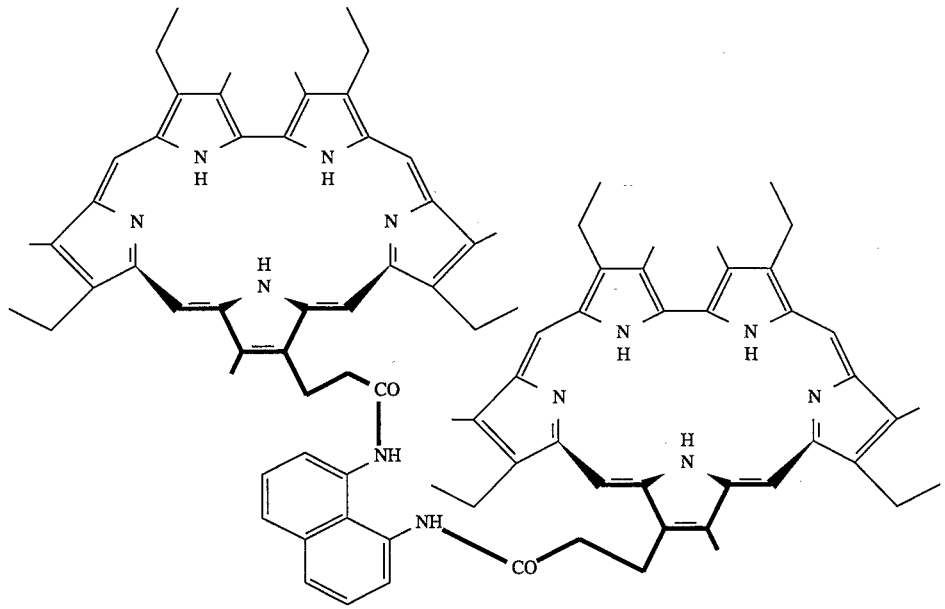

21

22
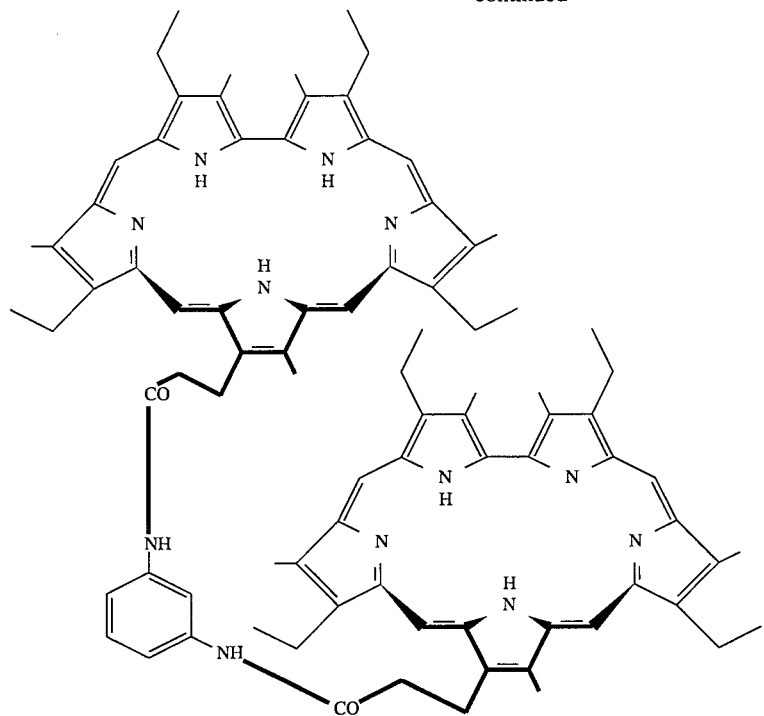
23
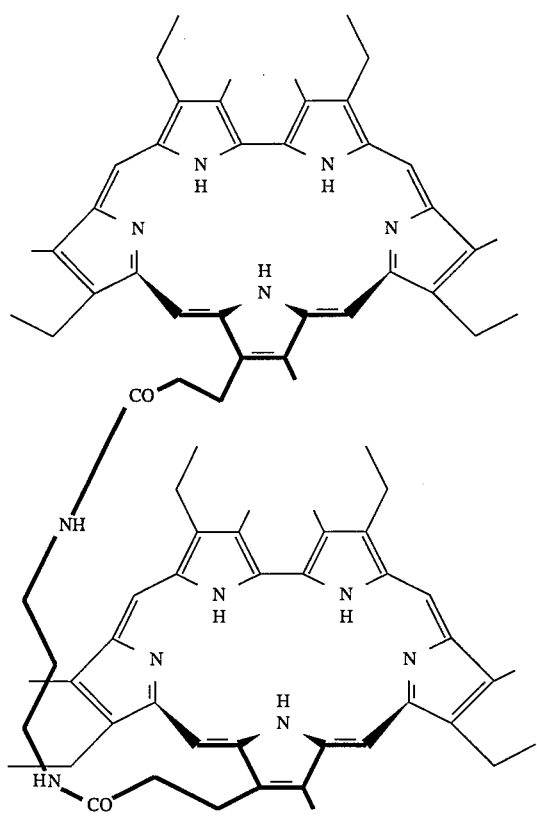

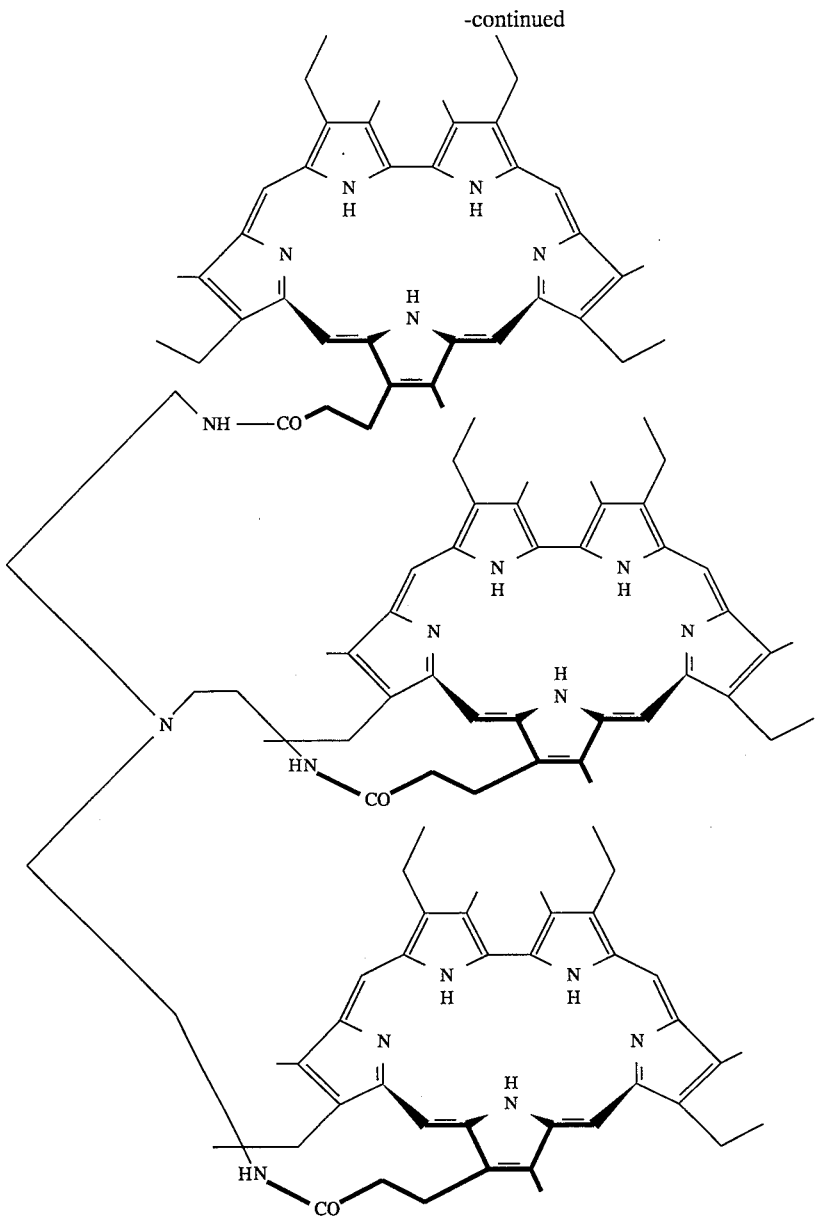

24

Sapphyrin multimers have been prepared by the condensation of sapphyrin mono and bis acids with amino groups as spacer units. As di- and tri-amino spacers, ethylenediamine, 1,3-diaminopropane, 1,3- and 1,4-phenylenediamine, diaminonaphthalenes and anthracenes, for example, have been used in the synthetic approach. Sapphyrin trimers were built in a one-step reaction, in which 3 molar equivalents of sapphyrin mono acid were combined with a trisamino component, e.g. tris(aminoethyl)amine, in very high yield.

For the coupling reaction, a variety of different methods have been used. These include, for example, acid chloride, O-acylurea, mixed anhydride and N-acylimidazole, which were found to be particularly successful. The synthetic methodology employed was essentially the same as that developed to prepare sapphyrin-nucleobase conjugates (as disclosed in parent application U.S. Ser. No. 07/964,607). It is important to emphasize that the synthesis of both the sapphyrin-nucleobase conjugates and the sapphyrin oligomers and polymers may be readily performed using a standard automated oligonucleotide synthesizer.

The present inventors have prepared dimers and trimers of sapphyrins and have proven them to be very efficient recognition species for nucleotides, monophosphates, diphosphates and triphosphates. The formation of noncovalently bonded complexes between sapphyrin oligomers and a nucleotide allows the transport of nucleotide mono-, di- and triphosphates across cell membranes to occur at physiological pH. This will likely be of direct use in the transport of antiviral triphosphates to mammalian cells, especially for the treatment of AIDS.

Any of the novel sapphyrins disclosed in parent application U.S. Ser. No. 07/964,607 may be employed, in any combination, in the synthesis of novel sapphyrin multimers. The synthetic approach developed is equally suitable to the use of one or more novel sapphyrin derivatives as starting materials as it is to the use of known sapphyrins.

Sapphyrin polymers contemplated by the present invention include those compounds resulting from the polymerization of monomeric units, by various types of processes other than those using a resin. For example, radical polymerization of olefin-substituted sapphyrin may be employed to give a polyethylene type of polymer. Alternatively, polycondensation of sapphyrin bis acid with sapphyrin diamine could be used to give a polyamide type of polymer, or polycondensation of sapphyrin bis acid with sapphyrin bis alcohol may be employed resulting in a polyester type of polymer. In all of these cases, sapphyrin-based polymers may be prepared both with and without covalently bonded nucleobases. Examples of sapphyrin polymers are 26A, 26B and 27.

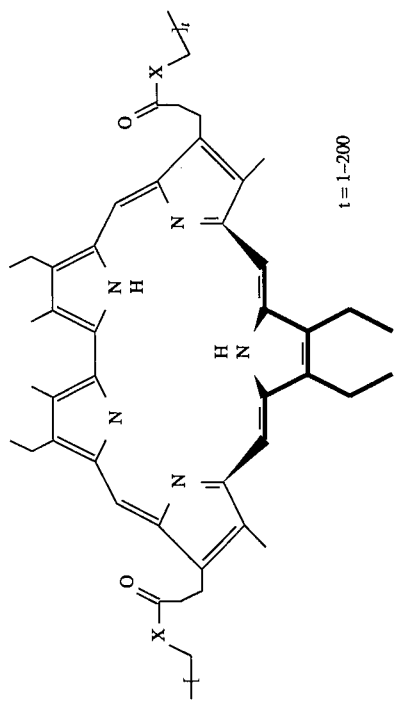
26A X = NH
26B X = O
t = 1-200
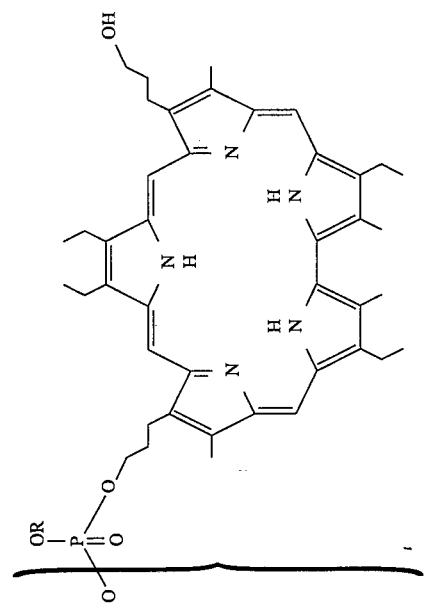
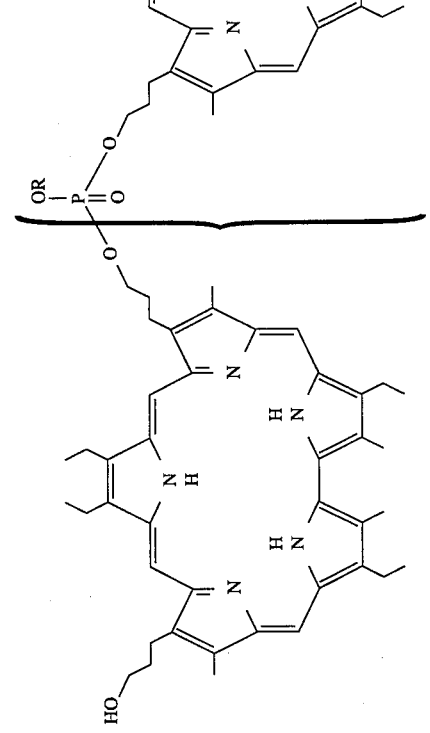
t = 1-200
R = H or ALKYL Linear sapphyrin trimer 14 may be prepared as shown in Scheme 1.

SCHEME 1
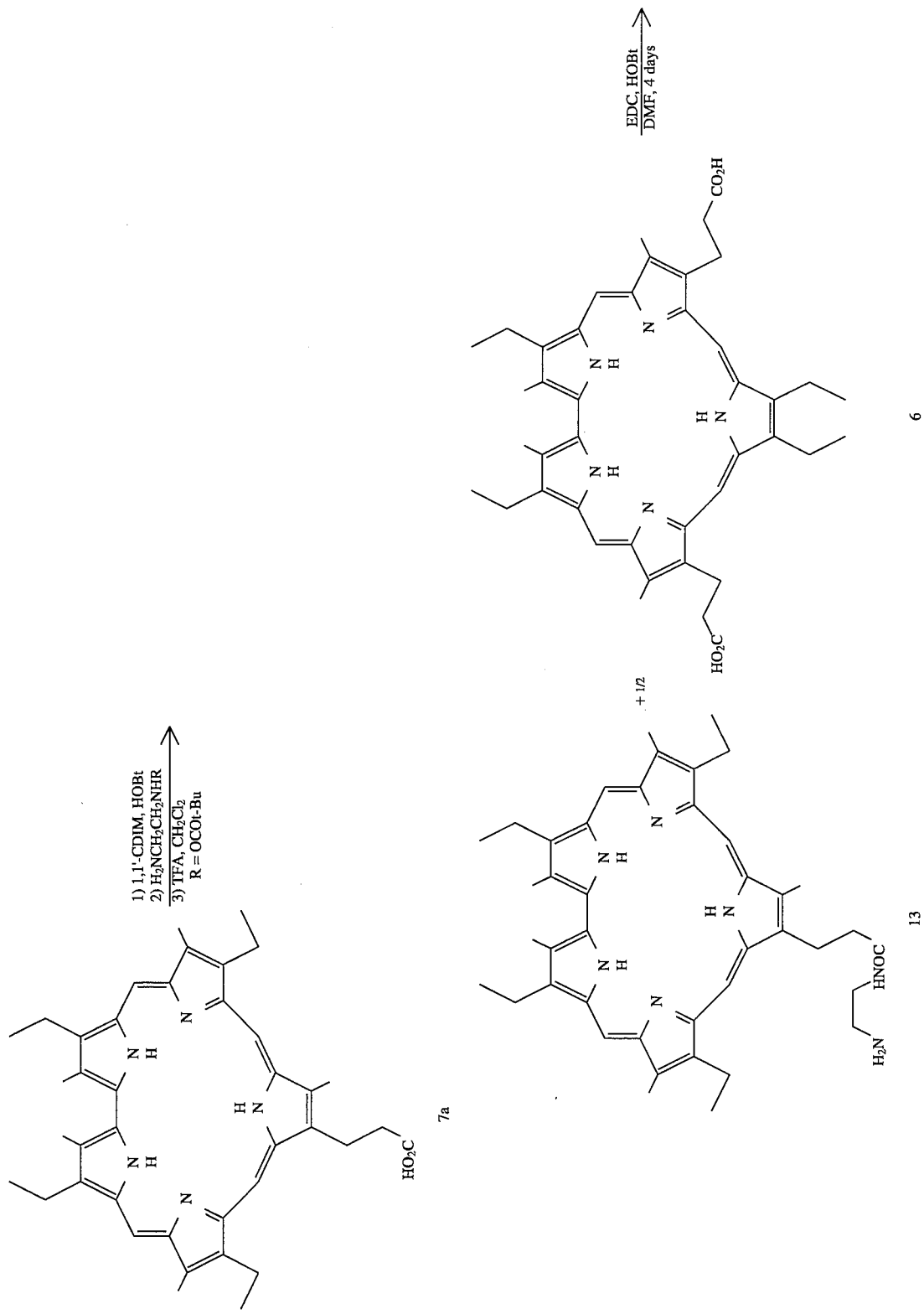

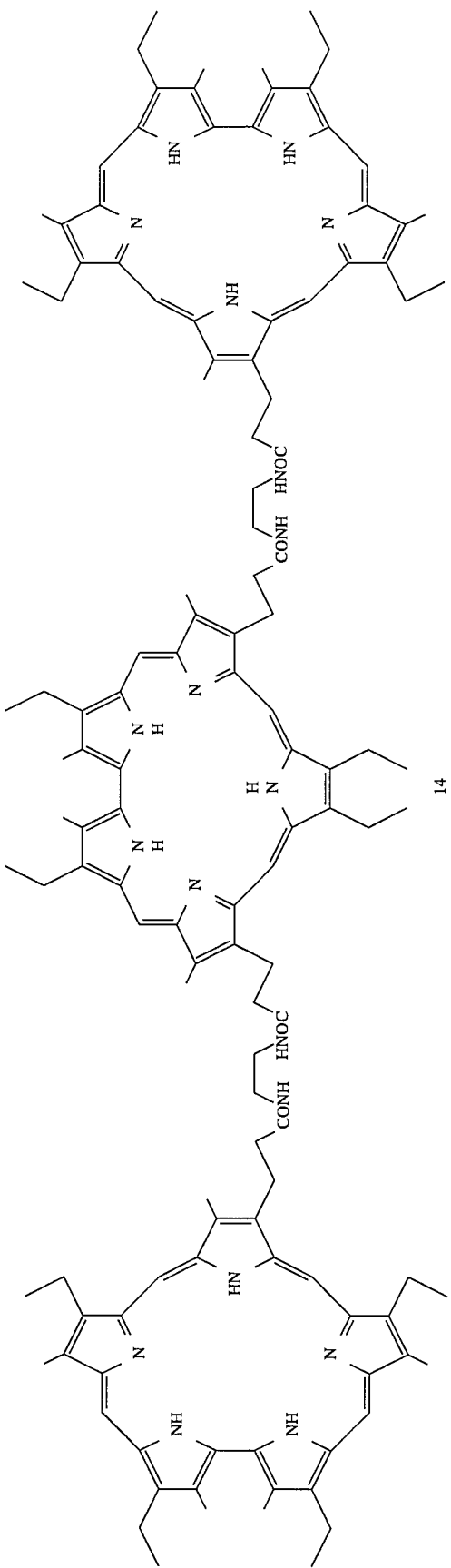

Two alternative methods for the preparation of 14 are shown in Schemes 2 and 3.
SCHEME 2
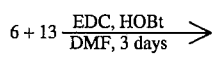
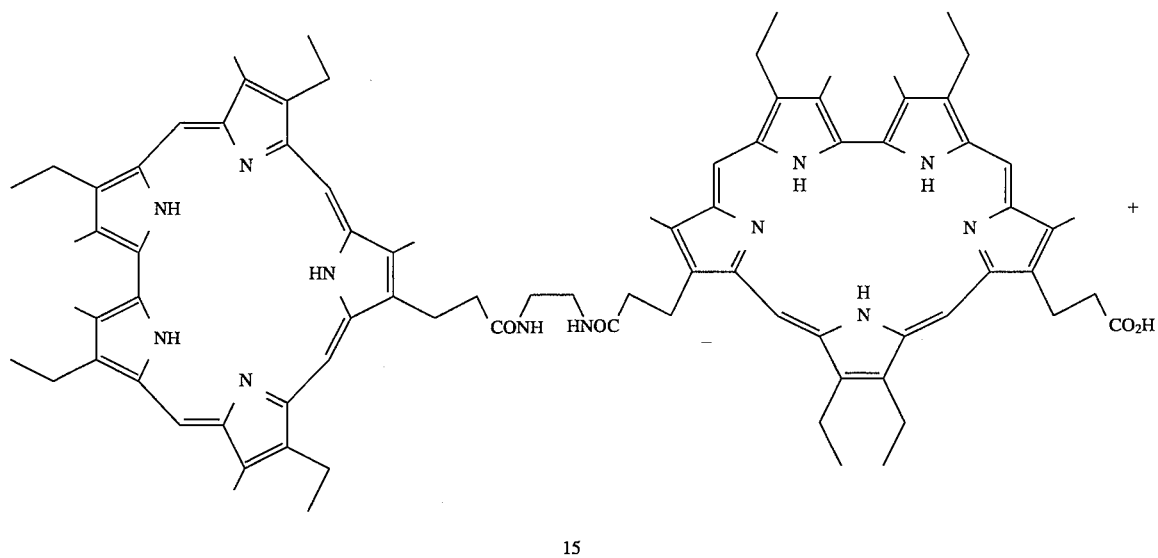
15
13 $\xrightarrow{\text{EDC, HOBt}}_{\text{DMF, 3 days}}$ 14
SCHEME 3
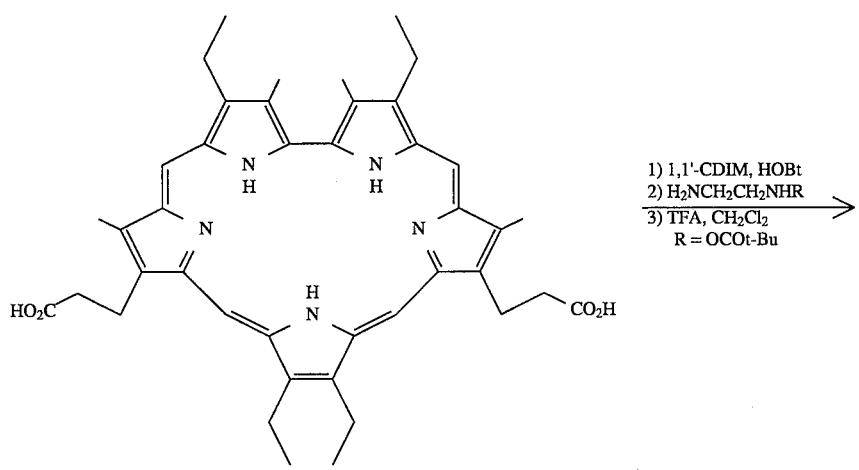
1) 1,1'-CDIM, HOBt
2) $H_2NCH_2CH_2NHR$
3) TFA, $CH_2Cl_2$
   R = OCOt-Bu -continued
SCHEME 3
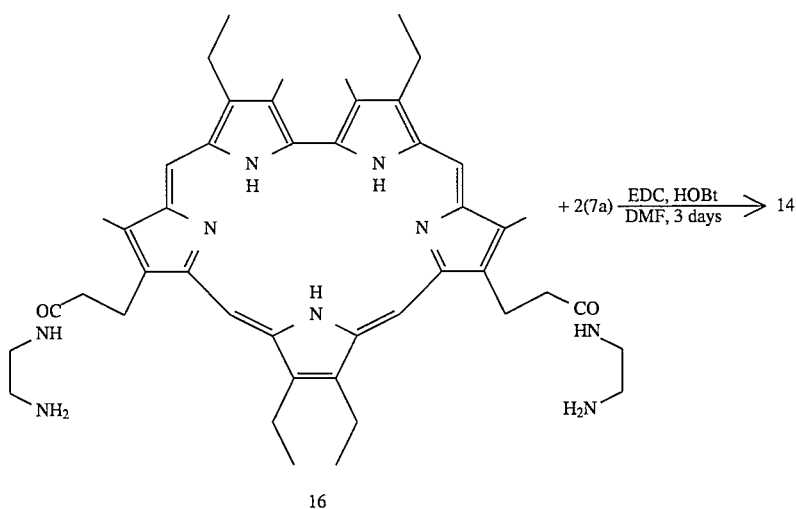
The synthesis of cyclic trimer 36 is accomplished as shown in Scheme 4, and Scheme 5, part 1 and 2.
SCHEME 4
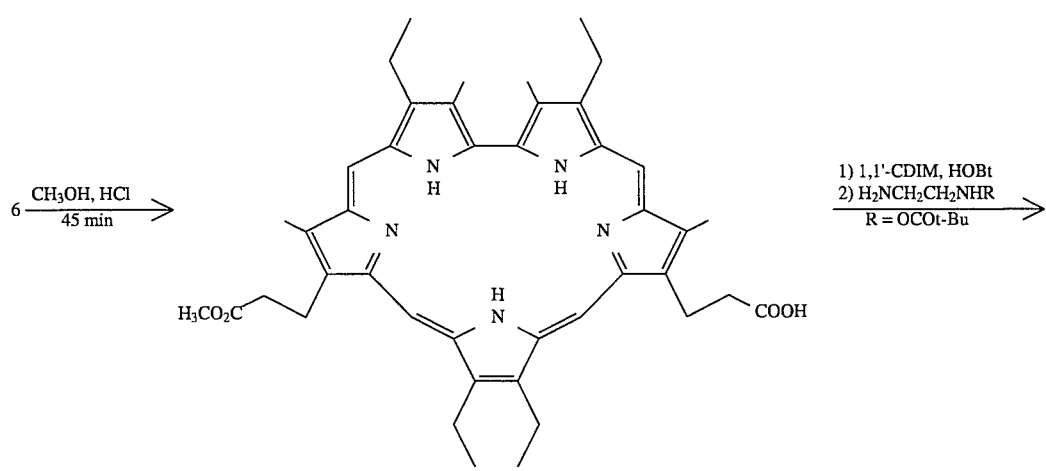

-continued
SCHEME 4
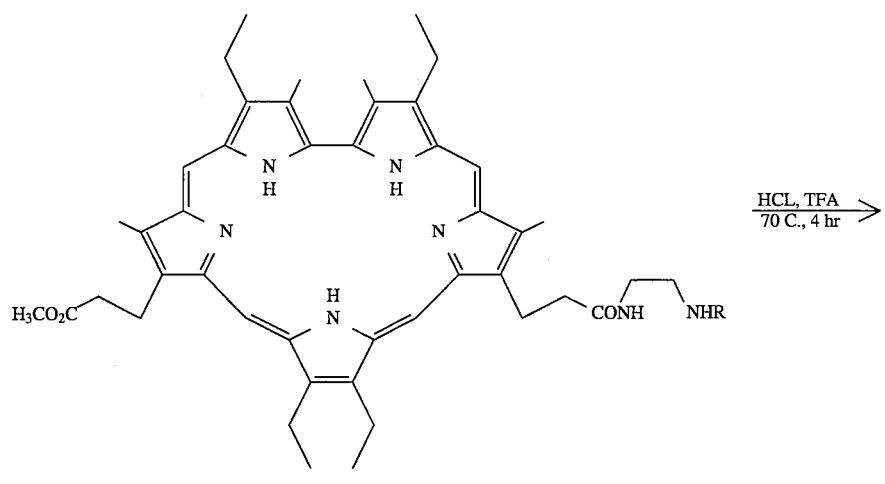
31
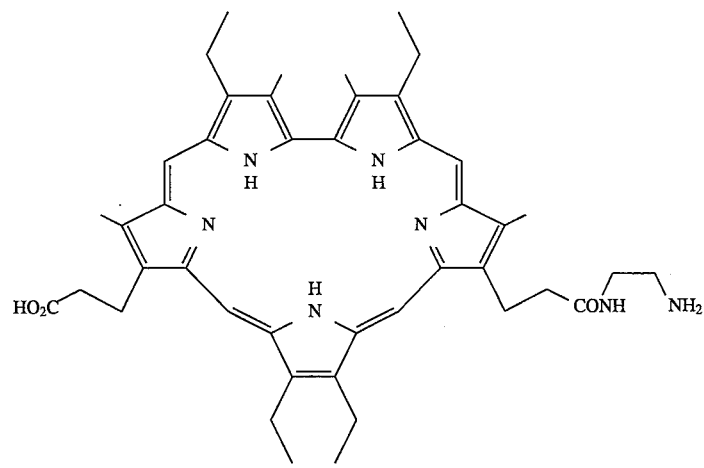
32

SCHEME 5, PART 1
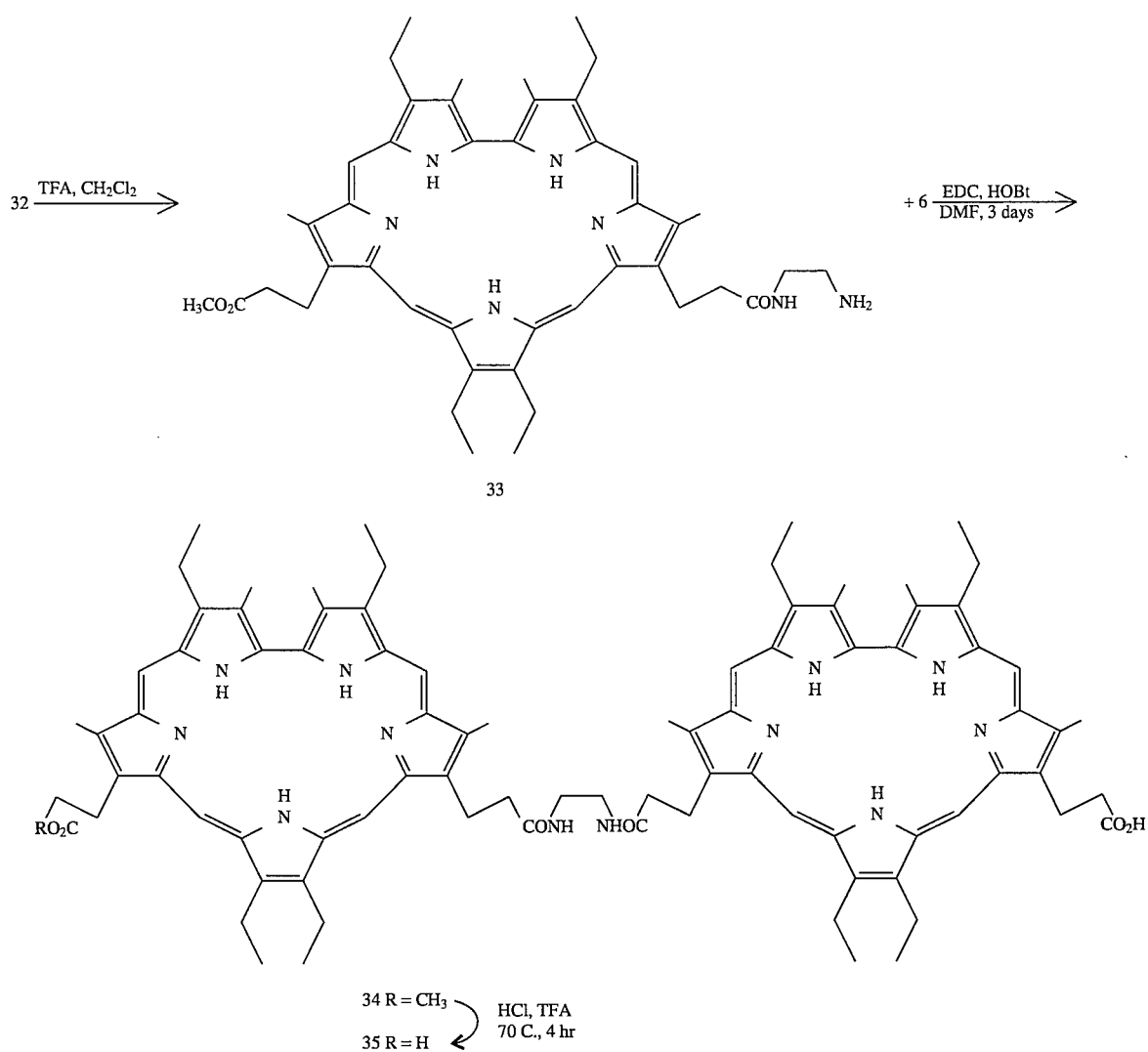

SCHEME 5, PART 2
35 + 16 $\xrightarrow{\text{EDC, HOBt}}_{\text{DMF, 3 days}}$
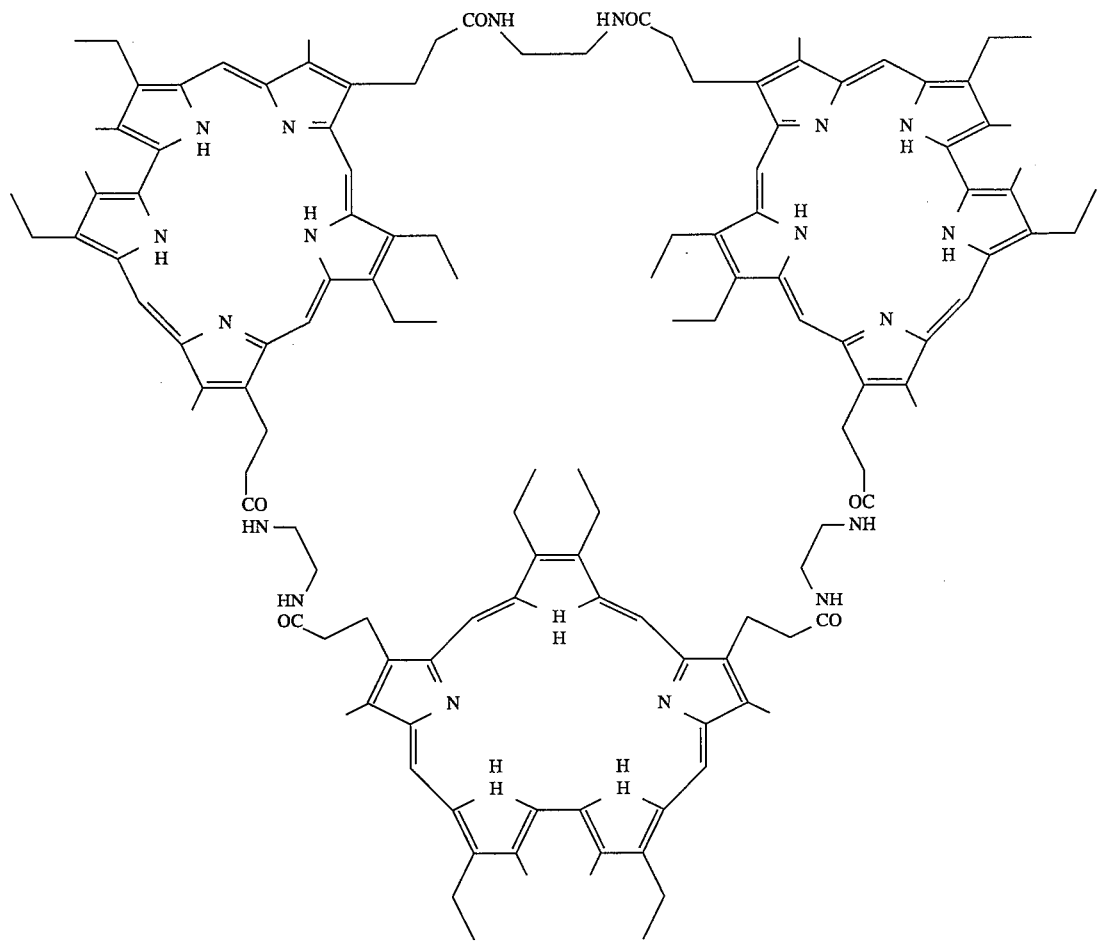
36
The synthesis of tethered sapphyrin tetramer 25 is described in Example 4, the structure is as follows.

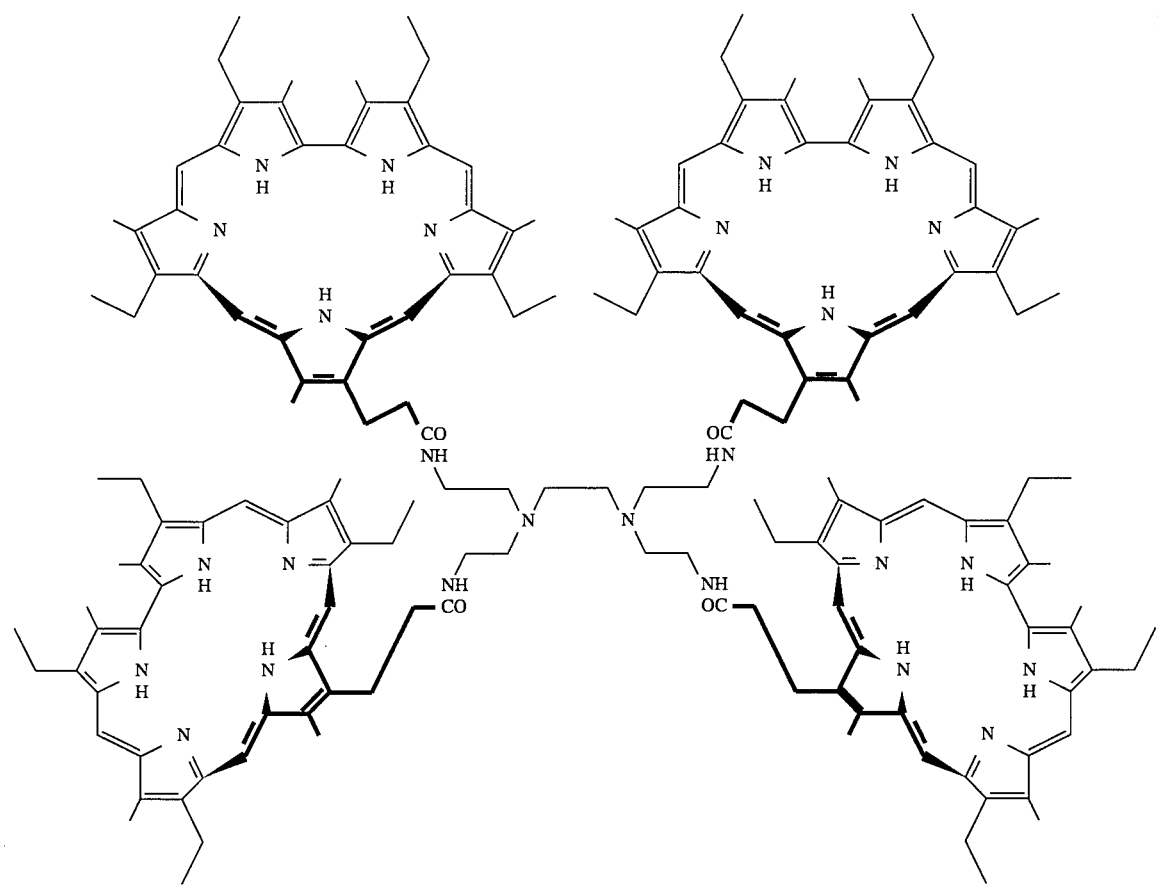

The synthesis of cyclic dimer 19 is described in Example 2, the structure is as follows.

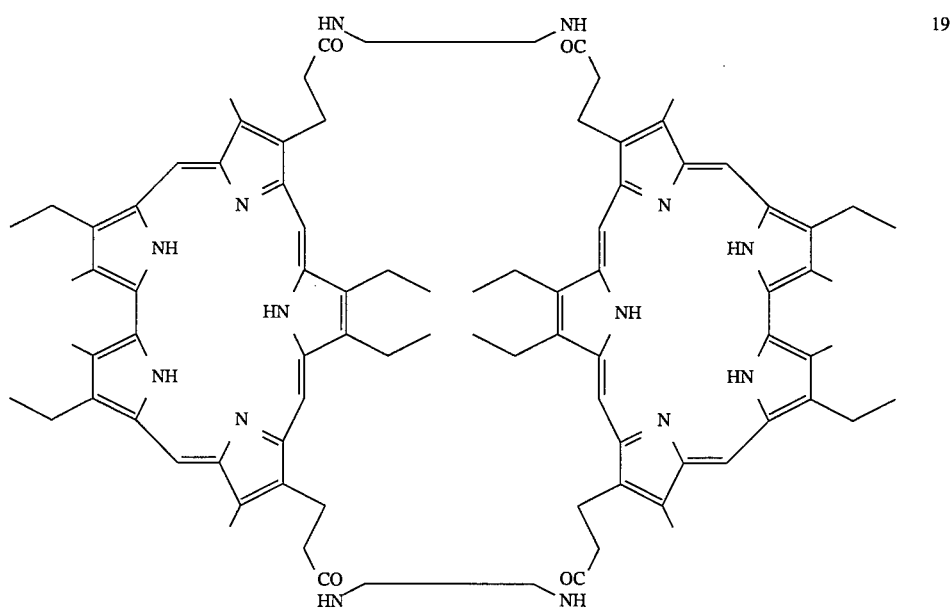

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

SYNTHESIS OF SAPPHYRIN DERIVATIVES HAVING A CARBOXY 7a, AN ESTER 7b, OR AN ACYL GROUP 7c, FOR USE AS PRECURSORS

The synthesis of the precursor 3,8,17,22-tetraethyl-12-(carboxyethyl-2,7,13,18,23-pentamethylsapphyrin, structure 7a, is a two-part procedure requiring the preparation of the ester 3,8,17,22-tetraethyl-12-(methoxycarbonylethyl)-2,7,13,18,23-pentamethylsapphyrin, structure 7b, and subsequent hydrolysis to the sapphyrin acid of general structure 7a. Ester 7b was prepared in accord with the general optimized procedure for the production of substituted sapphyrins[4a], incorporated herein by reference. 4,4'-Diethyl-5,5'-diformyl-3,3'-dimethyl-2,2'-bipyrrole (272 mg, 1.0 mmol) and 2,5-bis(5-carboxy-3-ethyl-4-methylpyrrol-2-yl-methyl)-3-methoxycarbonylethyl-4-methylpyrrole (523 mg, 1.0 mmol) were condensed to give this desired sapphyrin product in 75.4% yield (0.490 g).

$^1$H NMR (300 MHz, CDCl$_3$): δ=−4.78 (1H,s,NH), −4.76 (1H, s, NH), −4.32 (1H,s, NH), −4.13 (2H,s, NH), 2.35–2.43 (12H,m, CH$_2$CH$_3$), 3.85 (2H, t, CH2CH$_2$CO$_2$CH$_3$), 3.99 (3H,s, CH$_3$), 4.29 (6H, s, CH$_3$), 4.38 (3H,s, CH$_3$), 4.44 (3H,s, CH$_3$), 4.67–4.74 (8H, m, CH$_2$CH$_3$), 5.22 (2H, t, CH$_2$CH$_2$CO$_2$CH$_3$), 11.82 (1H,s,meso-H), 11.85 (1H,s,meso-H), 11.88 (2H,s,meso-H). $^{13}$C NMR (75 MHz, CDCl$_3$): δ=12.7, 13.1, 15.9, 17.8, 17.9, 21.0, 23.0, 37.1, 52.1, 91.5, 92.0, 98.3, 98.4, 126.9, 127.0, 129.5, 129.6, 130.2, 132.7, 132.8, 134.7, 135.3, 135.5, 136.6, 136.7, 137.7, 139.1, 141.5, 141.7, 173.3. HRMS: Calcd. for C$_{41}$H$_{49}$N$_5$O$_2$: 643.3886. Found 643.3887.

Sapphyrin acid 7a was prepared as follows: a ca. 1:1 v.v. mixture of trifluoroacetic acid and conc. hydrochloric acid (10 mL for 100 mg of starting sapphyrin 7b) was used to hydrolyze the ester 7b. The reaction was run at 50° C. for 2 days after which time the desired sapphyrin acid product 7a was obtained as its bis HCl adduct. After drying in vacuo, this protonated product was purified by column chromatography on silica gel (methanol 5% in dichloromethane, eluent). The yield was ca. 95%.

$^1$H NMR (300 MHz, CDCl$_3$): δ=−5.84 (2H, bs, NH), −5.35 (3H, bs, NH), 2.20 (12H, t, CH$_3$CH$_2$), 3.23 (2H, t, CH$_2$CH$_2$CO$_2$H), 4.03 (3H,s, CH$_3$), 4.15 (6H,s, CH$_3$), 4.23 (3H,s, CH$_3$), 4.41 (3H,s, CH$_3$), 4.65 (4H, q, CH$_2$CH$_3$), 4.74 (4H, q, CH$_2$CH$_3$), 4.79 (2H, m, CH$_2$CH$_2$CO$_2$H), 11.42 (2H,s,meso-H), 11.55 (1H,s,meso-H), 11.58 (1H,s,meso-H). $^{13}$C NMR (75 MHz, CDCl$_3$): δ12.7, 12.9, 14.3, 15.9, 17.7, 17.9, 20.6, 20.9, 22.8, 36.5, 36.7, 61.9, 91.6, 98.1, 120.7, 120.9, 125.4, 125.4, 127.3, 129.1, 129.2, 130.0, 132.7, 132.8, 134.8, 134.9, 135.2, 135.4, 135.6, 135.7, 136.1, 136.8, 136.9, 137.0, 137.7, 139.31, 141.4, 141.8, 141.8, 174.4. FAB MS, m/e (rel intensity): 631 (48, [MH$_2$]$^+$), 630 (100, [MH]$^+$), 629 (52, M$^+$); HRMS: Calcd. for C$_{40}$H$_{47}$N$_5$O$_2$: 629.3730. Found 630.3798 ([MH]$^+$); for C$_{40}$H$_{48}$N$_5$O$_2$ [MH]$^+$: Calcd. 630.3808.

The sapphyrin acid 7a, as prepared above (63 mg, 0.1 mmol), was dissolved in 10 mL of dry dichloromethane under argon. Oxalyl chloride (0.2 mL) was added followed by 0.03 mL of DMF. The reaction mixture was stirred at room temperature for 3 hours under argon and then evaporated to dryness in vacuo to give the corresponding sapphyrin acid chloride 7c.

EXAMPLE 2

PREPARATION OF LINEAR AND CYCLIC SAPPHYRIN DIMERS

The present example describes the preparation of linear and cyclic sapphyrin dimers. Sapphyrin monoacid 7a (126 mg, 0.2 mmol) was converted to acid chloride 7c as described hereinabove. A solution of the acid chloride in dry dichloromethane (20 mL) was slowly added to a solution of 0.1 mmol of an aromatic bis(amino)

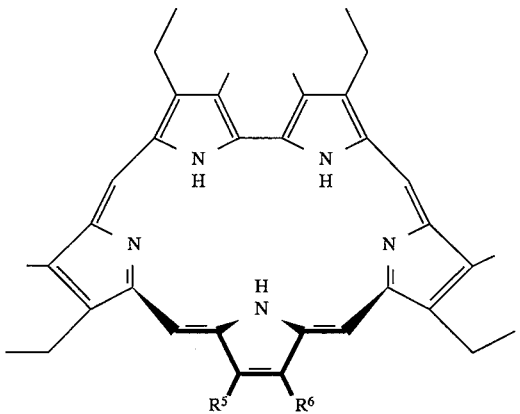

STRUCTURES:
1a. R$^5$ = R$^6$ = CH$_2$CH$_3$
7a. R$^5$ = CH$_2$CH$_2$CO$_2$CO$_2$H; R$^6$ = CH$_3$
7b. R$^5$ = CH$_2$CH$_2$CO$_2$CH$_3$; R$^6$ = CH$_3$
7c. R$^5$ = CH$_2$CH$_2$COCl; R$^6$ = CH$_3$ compound in dry dichloromethane (20 mL), which contained 5 mg 4-dimethylaminopyridine and 0.3 mL of dry pyridine. The reaction mixture was stirred 48 hours at room temperature, then washed with water, the organic phase was dried with magnesium sulfate and evaporated. The product was isolated by column chromatography on silica gel in dichloromethane with 2–10% of methanol as the eluent. Reaction with 1,8-diaminonapthalene (0.1 mmol, 15.8 mg) gave 80 mg (57.89%) of product 21.

FAB MS m/e (rel. intensity) 1382 (67, [MH]$^+$), 1381 (56, [M]$^+$). HRMS Calcd. for C$_{90}$H$_{100}$N$_{12}$O$_2$: 1380.80916. Found 1380.8093. Reaction with m-phenylenediamine (0.1 mmol, 10.8 mg) gave 69 mg (51.80%) of product 22. FAB MS m/e (rel. intensity) (78, [MH]$^+$), 1332 (65, [M]$^+$). HRMS Calcd. for C$_{86}$H$_{98}$N$_{12}$O$_2$: 1330. 79352. Found 1330. 79349.

Preparation of 1,3-bis[12-aminocarbonylethyl-(3,8,17,22-tetraethyl-2,7,13,18,23-pentamethylsapphyrin)]propane 23:

Method A. (via DeC coupling)

Reaction of sapphyrin monocarboxylic acid 7a with 1,3-diaminopropane was carried out using DCC as the coupling reagent. Sapphyrin acid 7a (126 mg, 0.2 mmol) was dissolved in dry dichloromethane under argon. The resulting solution was then cooled by ice to 0° C. Dicyclohexylcarbodiimide (0.25 g) was added along with 5 mg of hydroxybenzotriazole. The resulting reaction mixture was stirred at 0° C. for 30 minutes and then 1,3-diaminopropane (7.4 mg, 0.1 mmol) was added. Stirring was then continued for 30 minutes at 0° C. and then for 48 hours at room temperature. Following this, acetic acid (0.2 mL) was added and the reaction mixture stirred for 1 hour before dicyclohexylurea was filtered off. The product was purified via column chromatography using silica gel as the solid support and a gradient of 2–10% methanol in dichloromethane as the eluent. The yield of compound 23 (free-base form) was 96 mg (74.1%).

Vis (CH$_2$Cl$_2$ containing 3% CF$_3$CO$_2$H): $\lambda_{max}$ (nm) 449.0, 623.0, 681.0 FAB MS m/e (rel. intensity): 1298 (67, [M H$_+$]), 1299 (60, [M H$_2$]$^+$). HRMS: Calcd. for C$_{83}$H$_{101}$N$_{12}$O$_2$ [M H]$^+$: 1297.8170, found 1297. 8195.

Method B. (via acid chloride)

The sapphyrin acid 7a (63 mg, 0.1 mmol) was converted to its corresponding acid chloride (7c) via the method described hereinabove. The sapphyrin acid chloride was then redissolved in dry dichloromethane (20 mL) and slowly added to a solution of 1,3-diaminopropane in dry dichloromethane that contained 5 mg of 4-dimethylaminopyridine and 0.3 mL of dry pyridine. The resulting reaction mixture was stirred 48 hours at room temperature and washed with water. The remaining organic phase was dried over magnesium sulfate and evaporated to dryness. Product 23 (77% yield) was then isolated as described in Method A.

In general, the best yields ($\geq$70%) were obtained when the sapphyrin acid chloride 7c was used; however, the corresponding acylimidazole, mixed anhydrides, and activated esters could also be used.

Synthesis of Mono- and Bis-saccharide-Substituted Sapphyrins:

In general, saccharide-substituted sapphyrins were prepared by the reaction of an activated bis(sapphyrin) mono- or bis-acid and a polyhydroxy-amino component.

The synthesis of bis(sapphyrin) bis(acid) 35 is described in Example 3. This dimer may be further activated (via conversion to its acid chloride, a carbodiimide derivative, an NHS ester, or mixed anhydride) and reacted with an aminosaccharide derivative (or a protected form thereof) to give the corresponding sapphyrin glycosamides.

Bis(sapphyrin) monoacid 15 (Example 3) (0.1 mmol) was dissolved in 5 mL of dry DMF. Then, 1,1'-carbonyldiimidazole was added (0.2 mmol) and the reaction mixture stirred at room temperature for 2 hours. A solution of D-glucosamine.HCl (0.2 mmol) in 3 mL of water containing 0.3 mL of pyridine was then slowly added. The resulting reaction mixture was stirred for 4 days before being worked up in accord with the following procedure: Sodium bicarbonate (5 mL of a saturated aqueous solution) was first added. Then after 5 min, the resulting precipitated product (15c) was filtered off, washed with cold water (3 mL) and dried. Yield of product 15c is 64.5%. (The structure of 15c is not shown, however, 15c is structure 15 where the carboxyl group is replaced with CO—NH—D-glucosamine) Characterization data: FAB HR MS: Calcd for C$_{90}$H$_{11}$N$_{13}$O$_8$ ([M+H3]$^+$): 1502.87562; found: 1502.88245. UV-Vis ($\lambda_{max}$, H$_2$O, pH 7.0): 420 444 623 675.

Preparation of Bis(Sapphyrin) Gluconamides: In general, the activated bis(sapphyrin) monoacid (15) described in Example 3 was reacted with 1-amino-1-deoxy-D-sorbitol (or, in general, any D-glucamine in DMF-water (or aqueous buffer, pH 7.5–9) mixtures to give the sapphyrin gluconamides. Here, activation was effected using carbodiimide derivatives such as EDC or 1,3-diisopropylcarbodiimide or via the use of mixed anhyrides.

Bis(sapphyrin)-D-glucamide 15b. Bis(sapphyrin) monoacid 15 (0.1 mmol) was dissolved in dry DMF (5 mL) and cooled to 0° C. EDC (96 mg, 5 mmol) was then added together with 5 mg of 1-hydroxybenzotriazol. The resulting solution was stirred with external ice bath cooling for 1 hour. At this juncture, the chosen D-glucamine [in this case, 1-amino-1-deoxy-D-glucitol; alternative name: 1-amino-1-deoxysorbitol)] (108.7 mg, 6 mmol) in water (3 mL) and 4-dimethylaminopyridine (3 mg) were slowly added. Following this addition, the reaction mixture was stirred with cooling for 1 additional hour before being stirred for 7 more days at r.t. Work up consisted of adding 3 mL of saturated solution of sodium bicarbonate and then filtering off the resulting precipitate 5 minutes later. The resulting product 15b was washed with cool water (3 mL) and dried. Yield of 15b 110.6 mg (73.3%). (The structure of 15b is not shown, however, 15b is structure 15 where the carboxyl group is replaced with CO—NH—D-glucamine. Characterization data: FAB MS: Calcd for C$_{90}$H$_{115}$N$_{13}$O$_8$ ([M+H$_3$]$^+$): 1505.899159; found 1505.900165. UV-Vis ($\lambda_{max}$, H$_2$O, pH 6, bis(tris)buffer): 417 444 623 675.

A cyclic sapphyrin dimer 19 may be prepared by reacting 6 and 16 or, alternatively, reacting 32 with EDC, HOBt and DMF for about 3 days.

EXAMPLE 3

PREPARATION OF TETHERED, LINEAR AND CYCLIC SAPPHYRIN TRIMERS

Tethered, linear and cyclic sapphyrin trimers were synthesized using similar coupling procedures as described above for the sapphyrin dimers. Thus, sapphyrin monoacid 7a (189 mg, 0.3 mmol) was coupled (DCC method, 0.75 g) with tris(2-aminoethyl)amine (14.6 mg, 0.1 mmol) giving 160 mg (80.73%) of tethered sapphyrin trimer 24. FAB MS m/e (rel. intensity) 1983 (36, [MH]$^+$), 1982 (32, (M]$^+$). HRMS Calcd. for C$_{126}$H$_{153}$N$_{19}$O$_3$: 1980.240296. Found 1980.240289.

A further linear sapphyrin trimer 14 was prepared as follows. Proton and $^{13}$C NMR spectra were recorded on General Electric QE-300 spectrometer. Fast atom bombardment mass spectra (FAB MS) were obtained using a Finnigan-MAT TSQ-70 instrument and 3-nitrobenzyl alcohol matrix. All solvents and reagents were of reagent grade quality, purchased commercially, and used without further purification. Merck type 60 (230–400 mesh) silica gel was used for column chromatography. Thin layer chromatography (TLC) was performed on silica gel plates purchased from Whatman, Inc.

3,12,13,22-Tetraethyl-8,17-di (carboxyethyl)-2,7,18,23-tetramethylsapphyrin 6 (Sessler et al., JACS, 112:2810, 1990) and 3,8,17,22-Tetraethyl -12-[(carboxyethyl)-2,7,13, 18,23-pentamethylsapphyrin 7a (reference 12 and Example 1) were prepared as described. t-Butoxycarbonylaminoethylamine was prepared according Tarbel et al. (PNAS, 69:730, 1972).

3,8,17,22-Tetraethyl-12-[(aminoethyl)-aminocarbonylethyl]-2,7,13,18,23-pentamethyl-sapphyrin 13. Sapphyrin acid 7a (252 mg, 0.4 mmol) was dissolved in 10 mL of dry DMF. 1,1'-Carbonyldiimidazole (1,1'-CDIM) (130 mg, 0.8 mmol) and 1-hydroxybenzotriazole hydrate (HOBt) (10 mg) were added and the solution was stirred for 2 h at room temperature. A solution of t-butoxycarbonylaminoethylamine (128 mg, 0.8 mmol) in 2 ml of dry DMF was added all at once. The resulting solution was stirred for20 h after which solvent was evaporated in vacuo. The protected aminosapphyrin was purified by column chromatography on silica gel using methanol, 2–10% in dichloromethane as the eluent. To deprotect, it was dissolved in a mixture of dry dichloromethane (5 mL) and dry trifluoroacetic acid (5 mL) and stirred for 8 h. Solvent was evaporated in vacuo. The yield of 13 obtained this way was 208 mg (ca. 78%).

$^1$H NMR (free base) (300 MHz, CDCl$_3$): δ=–2.76 (3H, bs,NH), 1.93 (12H, m, CH$_3$CH$_2$), 2.69 (2H,bs CH$_2$), 3.02 (2H,bs,CH$_2$), 4.27 (15H,m, CH$_3$), 4.39 (10H,m, CH$_2$), 4.61

(2H,bs,NH$_2$), 10.19 (1H,s,meso-H), 10.58 (1H,s,meso-H), 10.62 (1H,s,meso-H), 10.67 (1H,s,meso-H). $^{13}$C NMR (free base) (75 MHz, CDCl$_3$ with 10% Cd$_3$OD): δ=12.05, 12.11, 12.24, 12.43, 15.88, 16.03, 17.54, 20.20, 20.26, 20.45, 20.51, 23.17, 38.91, 39.89, 41.14, 89.32, 89.72, 89.86, 94.41, 94.45, 95.38, 126.82, 132.15, 132.60, 132.86, 133.28, 133.56, 133.90, 134.03, 136.91, 137.27, 138.04, 139.92, 140.30, 142.34, 172.82. FAB MS, m/e (re. intensity): 671 (57, M$^+$), 670 (17, [M–H]$^+$). HRMS Calcd. for C$_{42}$H$_{52}$N$_7$O$_1$: 670.4233. Found 670.4218.

Synthesis of the bis(sapphyrin) monoacid 15.

Aminosapphyrin 13 and sapphyrin bisacid 6 were mixed in equimolar amounts. A DMF solution of 1.3 equivalents of EDC and 10 mg of HOBt were added at 0° C. The reaction mixture was stirred at that temperature for 30 min. and then allowed to warm to room temperature. Stirring was continued for 3–5 days (TLC control). Solvent was evaporated in vacuo. Product 15 was isolated in 45% yield by column chromatography on silica gel using methanol, 212% in dichloromethane, as the eluent. FAB MS m/e (re. intensity): 1344 (18, [M+2H]$^+$), 1343 (39, [M+H]$^+$), 1342 (36, M$^+$), HRMS Calcd. for C$_{84}$H$_{101}$N$_{12}$O$_4$: 1341.8068 Found 1341.6410.

Synthesis of sapphyrin trimer 14:

Sapphyrin trimer 14 was obtained in three different ways by means of coupling reactions in DMF. Aminosapphyrins and sapphyrin mono- and bisacids were mixed in the following ratios: 1 (13)+0.5 (6); or 1 (15)+1 (13); or 1 (7a)+0.5 (16) in 0.1 mmol amounts. DMF solution of 1.3 equivalents of 1-(3-dimethylaminopropyl)-3-ethyl carbodiimide hydrochloride (EDC) and 10 mg of 1-Hydroxybenzotriazole hydrate (HOBt) were added at 0° C. Reaction mixtures were stirred at that temperature for 30 min. and then allowed to warm to room temperature. Stirring was continued for 3–5 days (TLC control). Solvent was evaporated in vacuo. Product 14 was isolated in 400% yield by column chromatography on silica gel using methanol, 2–15% in dichloromethane, as the eluent.

$^1$H NMR (TFA salt) (500 MHz, CDCl$_3$ with 10% CD$_3$OD): δ1.9 (42H, m), 2.6 (8H, m), 3.1 (8H,bs), 4.2 (32H,m), 4.6 (42H,m) 1, 11.7 (12H, bs,meso -H). $^{13}$C NMR (TFA salt) (161 MHz, CDCl$_3$ with 10% CD$_3$OD): δ=12.42, 15.39, 17.28, 17.98, 20.45, 22.90, 23.40, 29.53, 37.92, 38.45, 90.76 (m), 97.56 (m). 110.33, 112.67, 126.96 (m), 127.30 (m), 128.63 (m), 129.30 (m), 131.88 (m), 132.10 (m), 134.52 (m), 135.50 (m), 136.70 (m), 137.07 (m), 138.27, (m), 139.93 (m), 141.62 (m), 142.36 (m), 154.36 (m), 172.51 (m). All signals have fine structure. FAB MS, m/e (rel. intensity): 1998 (63, [M+2H]$^+$), 1997 (77, [M=H]$^+$), 1996 (93, M$^+$), 1995 (76, [M–H]$^+$), 1994 (51, [M–2H]$^+$), 1993 (29, [M–3H]$^+$), 1992 (20, [M–4H]$^+$). HRMS Calcd. for C$_{126}$H$_{156}$N$_{19}$O$_4$: 1996.2353. Found 1996. 2366 (M$^+$).

3,12,13,22-Tetraethyl-8,17-di[(aminoethyl)aminocarbonylethyl]-2,7,18,23-tetramethylsapphyrin 16. The procedure described for the preparation of 13 was followed. Bisaminosapphyrin 16 was obtained in 72% yield. $^1$H NMR (free base) (300 MHz, CDCl$_3$): δ=5.94 (1H,s,NH), –5.54 (1H,s, NH), –5.48 (1H,s,NH), 1.59 (6H,m, CH$_3$CH$_2$), 1.96 (6H,t,C H$_3$CH$_2$), 2.96 (4H,m, CH$_2$), 3.17 (4H,m, CH$_2$), 3.96 (6H,s, CH$_3$), 4.01 (6H,s,CH$_3$), 4.29 (4H,q, CH$_2$CH$_3$), 4.56 (4H,q, C H$_2$CH$_3$), 4.77 (6H,m,CH$_2$CH$_3$), 8.17 (2H,t,NHCO), 9–18 (4H,bs,NH$_2$), 11.54 (2H,s,meso-H), 11.59 (2H,s,meso-H). $^{13}$C NMR (free base) (75 MHz, CD$_2$Cl$_2$ with 10% CD$_3$OD): δ=12.64, 15.40, 17.38, 18.31, 20.48, 20.54, 23.04, 36.82, 38.34, 39.14, 92.04, 98.74, 128.43, 129.01, 129.85, 132.53, 135.19, 135.45, 139.36, 139.59, 142.76, 144.35, 172.75.

FAB MS, m/e (rel. intensity): 774 (30,[M+2H]$^+$), 773 (76, [M+H]$^+$), 772 (100,M$^+$), 771 (29, [M–H]$^+$). HRMS Calcd. for C$_{46}$H$_{62}$N$_9$O$_2$: 772.5026. Found 772.5014.

A further sapphyrin cyclic trimer 36 was synthesized as follows.

3,12,13,22-Tetraethyl-8-(methoxycarbonylethyl)-17-carboxyethyl-2,7,18,23-tetramethyl-sapphyrin (30): Sapphyrin bisacid 6 (190 mg, 0.25 mmol) was dissolved in 50 ml of acetone, methanol (2 mL) and concentrated aqueous solution of HCl (1 mL) were added. The mixture was stirred for 2–6 hrs (formation of products was monitored by TLC). A saturated solution of sodium bicarbonate (3 mL) was added, acetone and methanol were evaporated and the residue extracted with 10% methanoldichloromethane solution. The organic layer was separated, dried with anhydrous sodium carbonate and evaporated. Monoprotected sapphyrin 30 was isolated by column chromatography on silica gel using methanol, 2–10% in dichloromethane, as the eluent.

$^1$H NMR (TFA salt) (300 MHz, CDCl$_3$): δ=–5.11 (1H,s, NH), 5.05 (1H,s,NH), –4.74 (1H,s,NH), 4.58 (1H,s,NH), 4.52 (1H,s,NH), 1.01 (2H,m), 1.19 (2H,m), 1.42 (2H,m), 2.1 (8H,bs), 2.24 (3H,s), 3.13 (2H, bs ), 3.59 (2H,bs), 3.68 (2H,bs), 4.04 (2H,bs), 4.13 (4H,bs), 4.26 (2H,bs), 4.59 (8H,m), 5.05 (2H,bs), 11.48 (1H,s,meso-H), 11.63 (3H,m, meso-H). $^{13}$C NMR (TFA salt) (75 MHZ, CDCl$_3$ with 10% CD$_3$OD): δ=12.63, 12.76, 13.86, 15.42, 17.33, 18.09, 20.65, 22.73, 36.69, 51.81, 90.99, 91.46, 98.34, 98.39, 127.58, 128.57, 129.22, 129.34, 129.47, 129.99, 130.78, 132.35, 132.42, 135.08, 135.15, 135.47, 135.99, 137.34, 137.63, 138.04, 138.14, 141.76, 141.86, 144.19, 143.46, 173.27. FAB MS m/e (rel. intensity): 704 (100, [M+2H]$^+$), 703 (36, [M+H]$^+$), 702 (77, M$^-$). HRMS Calcd. for C$_{43}$H$_{52}$N$_5$O$_4$: 702.4019. Found 702.3997.

3,12,13,22-Tetraethyl-8-[(t-butoxycarbonylaminoethyl)aminocarbonylethyl]-17-(methoxy-carbonylethyl)-2,7,18, 23-tetramethylsapphyrin 31: The general procedure for preparation of aminosapphyrins was followed, excluding the deprotection step. The yield of 31 obtained was 73%. $^1$H NMR (HCl salt) (300 MHz, CDCl$_3$): δ=1.16 (9H,s), 2.25 (12H,m), 2.77 (2H,bs), 3.01 (2H,bs), 3.27 (2H,m), 3.63 (2H,m), 3.79 (3H,s), 4.08 (3H,s), 4.09 (3H,s), 4.18 (3H,s), 4.26 (3H,s), 4.52 (4H,m), 4.70 (4H,m), 5.02 (4H,m), 5.86 (2H,m), 11.51 (4H,m). $^{13}$C NMR (HCl salt) (300 MHz, CDCl$_3$ with 10% CD$_3$OD): δ=12.71, 12.85, 12.90, 15.95, 16.18, 17.64, 17.72, 18.36, 18.41, 20.71, 22.69, 23.36, 27.90, 28.12, 36.82, 38.84, 39.34, 51.97, 78.88, 91.26, 91.91, 97.45, 97.57, 115.56, 115.81, 121.17, 123.03, 127.05, 128.49, 128.68, 129.31, 129.37, 129.54, 129.59, 132.03, 132.44, 134.44, 135.06, 135.20, 135.26, 138.11, 138.40, 138.48, 138.82, 143.28, 143.34, 143.69, 143.93, 144.16, 172.94, 173.17. FAB MS m/e (re. intensity): 846 (26, [M+2H]$^+$), 845 (66, [M+H]$^+$), 844 (98, M$^+$), 843 (26, [M+H]$^+$). HRMS Calcd. for C$_{50}$H$_{66}$N$_7$O$_5$: 844.5125. Found: 844.5131.

3,12,13,22-Tetraethyl-8-[(aminoethyl)-aminocarbonylethyl] -17-methoxycarbonylethyl-27,18,23-tetramethylsapphyrin (33):

Aminosapphyrin 33 was obtained in 82% yield from 31 by following general deprotection procedure. $^1$H NMR (FREE BASE) (300 MHz, CDCl$_3$ with 10% CD$_3$OD): δ=1.97 (2H,m), 2.10 (6H,m), 2.25 (6H,m), 3.42 (2H,m), 3.58 (2H,m), 3.67 (3H,s), 4.16 (6H,bs), 4.24 (3H,s), 4.27 (3H,s), 4.56 (4H,m), 4.76 94H,m), 5.03 (4H,m), 11.63 (1H,s,meso-H), 11.65 (1H,s,meso-H), 11.72 (1H,s,meso-H), 11.78 (1H,s,meso-H). $^{13}$C NMR (free base) (300 MHz, CDCl$_3$ with 10% CD$_3$OD): δ=12.65, 12.85, 15.84, 17.47, 17.57, 18.25, 18.31, 20.58, 20.72, 22.72, 23.39, 36.29, 36.79, 38.20, 38.66, 51.92, 90.97, 92.36, 97.48, 98.02, 122.62, 126.95, 128.46, 129.01, 129.43, 129.71, 132.22, 132.31, 132.42, 134.83, 135.17, 135.32, 137.92, 138.43, 138.56, 139.33, 142.69, 143.58, 144.51, 173.24, 173.69. FAB MS m/e (rel. intensity): 746 (42, [M+2H]$^+$), 745 (98, [M+H]$^+$), 744 (95, M$^+$), 743 (32, [M−H]$^+$). HRMS Calcd. for $C_{45}H_{58}N_7O_3$: 744. 4601. Found 744.4594.

Synthesis of sapphyrin 34.

Aminosapphyrin 33 and sapphyrin bisacid 6 were mixed in equimolar amounts. DMF solution of 1.3 equivalents of EDC and 10 mg of HOBt were added at 0° C. The reaction mixture was stirred at that temperature for 30 min. and then allowed to warm to room temperature. Stirring was continued for 3–5 days (TLC control). Solvent was evaporated in vacuo. Product 23 was isolated in 57% yield by column chromatography on silica gel using methanol, 2–12% in dichloromethane, as the eluent. FABS MS m/e (tel. intensity): 1416 (32, [M+3H]$^+$), 1415 (65, [M+2H]$^+$), 1414 (99, [M+H]$^+$), 1413 (98, M$^+$), 1412 (50, [M−H]$^+$). HRMS Calcd. for $C_{87}H_{105}N_{12}O$: 1413. 8280. Found 1413. 8299.

Synthesis of sapphyrin dimeric hisacid 35.

Compound 34 was dissolved in the mixture of TFA:HCL$_{conc}$=1:1 and the resulted solution was subjected to reflux at 70° C. for 5 h. Solvents were evaporated in vacuo. Compound 35 was obtained in 93% yield and used without further purification. FABS MS m/e (rel. intensity): 1401 (77, [M+3H]$^+$), 1400 (100, [M+2H]$^+$), 1399 (86, [M+H]$^+$), 1398 (42, M$^-$). HRMS Calcd. for $C_{86}H_{104}N_{12}O_6$ ([M+2H]$^+$): 1400.8202. Found 1400. 8199.

Synthesis of sapphyrin cyclic trimer 36.

Sapphyrin dimeric bisacid 35 and bisaminosapphyrin 16 were mixed in the equimolar amounts. DMF solution of 2.6 equivalents of EDC and 10 mg of HOBt were added at 0° C. Reaction mixture was stirred at that temperature for 30 min. and then allowed to room temperature. Stirring was continued for 3–5 days (TLC control), added. Solvent was evaporated in vacuo. Product 36 was isolated in 28% yield by column chromatography on silica gel using the mixture of methanol, (2–20%), TFA (1%), in dichloromethane, as the eluent. FAB MS m/e (rel. intensity): 2143 (46, [M+2H]$^+$), 2142 (64, [M+H]$^+$), 2141 (98, M$^+$), 2140 (68, [M−H]$^+$), 2139 (46, [M−2H]$^+$). HRMS Calcd for $C_{132}H_{166}N_{21}O_6$; 2141.3329. Found 2141.3349.

EXAMPLE 4

SYNTHESIS OF A TETHERED SAPPHYRIN TETRAMER

The present example provides for the synthesis of a tethered sapphyrin tetramer 25.

Preparation of sapphyrin 25:

Method A. (via diisopropylcarbodiimide coupling)

A reaction of sapphyrin monocarboxylic acid 7a with aliphatic (amino)$_n$ compounds (n=14) was carried with diisopropylcarbodiimide as a coupling reagent. Sapphyrin acid 7a (252 mg, 0.4 mmol) was dissolved in dry dichloromethane under argon. The resulting solution was then cooled by ice to 0° C. 1,3-Diisopropylcarbodiimide (0.126 g. 1 mmol) was added with 5 mg of 1-hydroxy-benzotriazole. The reaction mixture was stirred at 0° C. for 30 minutes and then tetrakis(2 aminoethyl)ethylenediamine (23.2 mg, 0.1 mmol) was added. The reaction mixture was stirred for 30 min. at 0° C. and 48 hours at room temperature. Acetic acid (0.2 mL) was added and the mixture stirred 1 hour. The product was then isolated by column chromatography on silica gel using dichloromethane containing 5–10% methanol as the eluent. Yield of pure compound 25 is 168 mg (62.7%).

FAB MS m/e (rel. intensity) 2679 (67, [MH]$^+$), 2680 (60, [MH$_2$]$^+$). HRMS Calcd. for $C_{170}H_{210}N_{26}O_4$ [MH$_2$]$^+$: 2679.70284. Found 2679.77100. $^1$H NMR (300 MHz, CDCl$_3$ with 5% CD$_3$OD): δ=1.74 (24H,m, CH$_2$CH$_3$), 1.85 (24H,m, CH$_2$CH$_3$), 2.61 (8H,m, CONHCH$_2$), 3.01 (12H, m, CONHCH$_2$CH$_2$N, NCH$_2$CH$_2$N), 3.40 (8H, t, CH$_2$CH$_2$CONH), 3.58 (24H,s,CH$_3$), 3.67 (12H,s,CH$_3$), 3.83 (18H, s,CH$_3$), 3.90 (6H,s,CH$_3$), 4.06 (16H,q, CH$_2$CH$_3$), 4.19 (16H, q,CH$_2$CH$_3$), 4.30 (8H, t,CH$_2$CH$_2$CONH), 9.85 (4h, S,methine), 10.05 (4H,s,methine), 10.24 (4H,s,methine), 10.32 (4H,s,methine). Vis 25 (free base), CH$_2$CL$_2$): λ$_{max}$: 428.0, 449.0, 620.0, 642.0, 667.0. Vis 25 (CH$_2$Cl$_2$ with 3% TFA): λ$_{max}$: 448.0, 623.0, 681.0.

Method B. (via acid chloride)

The sapphyrin monoacid 3,8,17,22-tetraethyl-12-(carboxyethyl-2,7,13,18,23-pentamethylsapphyrin 7a (63 mg, 0.1 mmol) was converted to its corresponding acid chloride via a standard procedure: The sapphyrin acid was dissolved in 25 mL of dry dichloromethane under argon. Oxalylchloride (0.2 mL) was then added, followed by 0.03 mL of DMF. The reaction mixture was stirred at room temperature for 3 h under argon and then evaporated in vacuo. The sapphyrin acid chloride so obtained was redissolved in dry dichloromethane (20 mL) and slowly added to a solution of the tetraamine; tetrakis (2-aminoethyl)-ethylenediamine (5.8 mg, 0.025 mmol), which contained 5 mg 4-dimethylaminopyridine and 0.3 mL of dry pyridine.

The resulting reaction mixture was stirred 48 hours at room temperature, then washed with water. The organic phase was dried with magnesium sulfate and evaporated. The product was isolated by column chromatography on silica gel using dichloromethane containing 2–10% of methanol and 1–3% TFA as the eluent. Product 25 was obtained in 56.9% yield.

EXAMPLE 5

PREPARATION OF SAPPHYRIN POLYMERS

For the preparation of polymers, sapphyrins with ethylene units could be used, as prepared by the elimination of acetoxy derivative, as well as sapphyrin bis acid, sapphyrin diamino- or dihydroxyderivatives. Sapphyrins bearing covalently attached nucleobases could also be used for the polymerization reactions.

Radical polymerization may be catalyzed by dibenzoylperoxide, or bisazaisobutyronitril in inert solvent at temperature 120°–200° C.

Polycondensation reaction: 3,12,13,22-Tetraethyl-8,17-bis(carboxyethyl-2,7,18,23-tetramethylsapphyrin (1 mmol) and 1,1'-carbonyldiimidazole (1.1 mmol) were mixed in diphenylether for 1 hour, then 3,12,13,22-tetraethyl-8,17-diaminoethyl-2,7,18,23-tetramethylsapphyrin (1 mmol) was added and the reaction was heated at 190°–250° C. for 2 hours. After cooling, dichloromethane was added. Polymeric sapphyrin structure 26A (where X=NH) was filtered off, and washed with water (50 mL) and methanol (50 mL).

Polymeric sapphyrin was obtained also by using sulfolan, hexamethylphosphortriamide as a solvent. The reaction could be also carried out without solvent.

The same procedure was followed using the sapphyrin dialcohol as a starting compound for the preparation of sapphyrin diacid structure 26B (where X=O).

To synthesize structure 27, it is contemplated that one would employ standard phosphoramidate chemistry.

The molecular weight (and, therefore, t) of sapphyrin polymers may be estimated by use of electrospray mass spectrometry which is applicable for molecular weights up to about 12,000. This determination may also be made using SEPHADEX® gel filtration (Sigma, St. Louis, Mo.), for example.

EXAMPLE 6

STEPWISE SYNTHESIS OF MULTIMERIC SAPPHYRIN-OLIGONUCLEOTIDE CONJUGATES

The present example provides synthetic procedures in which a sapphyrin multimer is inserted directly into a nucleic acid synthesis scheme, preferably on a solid support. Sapphyrin macrocycles were not known to be stable under the basic conditions employed in the synthesis of oligonucleotides. It was possible that the meso positions of sapphyrin would be unstable. Therefore, the stepwise synthesis of sapphyrin oligonucleotide conjugates presented herein was a surprising and unexpected result. The synthesis of sapphyrin-nucleobase conjugates is described in U.S. Ser. No. 07/964,607 and PCT/US93/09994, incorporated by reference herein.

It is contemplated that the stepwise synthesis provided herein may be performed manually or may be automated, and may be in a solution-phase or on a solid support. Solid support synthesis may be accomplished using an automated or a manual nucleic acid synthesizer. Common solid supports are CPG (control pore glass) and CPS (control pore silica). Other possible solid supports include polystyrene, polyamide/Kieselguhr, and cellulose paper. A preferred embodiment of this method is automated synthesis on a solid support. Attachment of a sapphyrin multimer to an oligonucleotide during stepwise synthesis obviates the need for a postmodification protocol and a second purification of the product. This results in an improved yield and greatly facilitates scale-up.

A sapphyrin multimer may be inserted into the synthesis scheme of an oligonucleotide in a variety of ways. Possible linkages include amide, phosphate, thioether, amino, and ether linkages. An amide linkage represents the reaction of an activated carboxylic acid derivative of a multimer and an amino linker attached to an oligonucleotide. Activation may be achieved in solution phase or on a solid support using DCC and NHS, EDC, or activated esters of NHS, nitrophenyl, pentachlorophenyl, acid anhydride, or sulfonyl chloride. In addition, for the solid support reaction, activation may be in the form of an acid chloride. A phosphate linkage represents the reaction of an activated phosphate derivative of a multimer and the 5' hydroxyl group on an oligonucleotide. The activated phosphate derivative may be a phosphoramidite, an H-phosphonate, a triester, or a diester.

Sapphyrin-oligonucleotide conjugates have been made using a direct coupling amide linkage method or by incorporation during oligonucleotide synthesis forming a 5' linkage via the H-phosphonate method as follows.

Direct coupling method (amide linkage):

Sapphyrinoligonucleotide conjugates with an amide linkage were formed on a solid support. Specifically, sapphyrin monoacid 1a (6.8 mg, 0.011 mmol, 50 eq) was dissolved in 2 mL of methylene chloride in a 4 mL glass vial with a small stir bar followed by cooling to 0° C. with an ice bath. Dicyclohexylcarbodiimide (4.5 mg, 0.022 mmol, 100 eq), dimethylaminopyridine (0.001 mg, catalytic amount), and N-hydroxysuccinimide (2.5 mg, 0.022 eq, 100 eq) were added to the solution which was then stirred for 30 min. Protected amino- derivatized oligonucleotide attached to CPG solid support (2.5 mg, 0.108 µmol, 1 eq) was added to the solution which was stirred overnight at room temperature. The solution was filtered and the conjugate attached to the CPG was washed once with methylene chloride and twice with methanol. The green solids were then suspended in conc. ammonium hydroxide for 4 h at room temperature after which the green solution was filtered and evaporated to afford the crude sapphyrinoligonucleotide conjugate. The conjugate could be purified by fplc on a $C_{18}$ column using acetonitrile/100 mM triethylammonium acetate, pH 7.0.

The coupling step in this case was done on a solid support although it may be done in solution. This procedure attaches sapphyrin to the 5' end of the oligonucleotide and could be modified to link macrocycles to the 3' end, or internal to an oligonucleotide.

Incorporation during oligonucleotide synthesis (phosphate linkage):

A monoprotected sapphyrin H-phosphonate was synthesized for incorporation during oligonucleotide synthesis. A sapphyrin-conjugate was synthesized in a solid-phase manual oligonucleotide synthesizer via the H-phosphonate method. The oligonucleotide was assembled on a solid support such as controlled pore glass (CPG) by a cycle of steps. The 5' end of the growing oligonucleotide was deprotected, the reaction phase was neutralized, and the activated monoprotected nucleotide H-phosphonate was coupled at the 5' end of the oligonucleotide. Derivatized sapphyrin was incorporated at the 5' end of the oligonucleotide during the last step of the synthesis in place of a nucleotide.

Specifically, the desired oligonucleotide was synthesized on a CPG solid support on a 0.2 µM scale. The derivatized sapphyrin was attached to the oligonucleotide on a manual oligonucleotide synthesizer (Cruachem PS 150 DNA Synthesizer, Sterling, Va.). The synthesis was run under argon (5 psi). Syringes were oven-dried and kept in a desiccator until use. The following sequence was used for coupling:

1. Wash—acetonitrile—2 min.
2. Deblock—3% dichloroacetic acid in methylene chloride—3 min.
3. Wash—acetonitrile—2 min.
4. Wash—acetonitrile/pyridine (1:1)—2 min.
5. Couple—4 mM derivatized sapphyrin (1 eq) in methylene chloride and 65 mM pivaloyl chloride in acetonitrile/methylene chloride (1:1)—30 µL solution alternating for 1.5 min.
6. Wait—15 min.
7. Wash—acetonitrile, acetonitrile/pyridine (1:1), acetonitrile—2 min, 1 min, 2 min.
8. Deprotect—3% dichloroacetic acid in methylene chloride—3 min.
9. Wash—acetonitrile, acetonitrile/pyridine (1:1)—2 min, 2 min.
10. Oxidize—0.1M iodine in water/pyridine/N-methylimidazole/THF (5/4/1/90), 0.1M iodine in water/triethylamine/THF (5/5/90)—2 min, 2 min.
11. Wash—acetonitrile/pyridine (1:1), acetonitrile, methanol—2 min, 1 min, 2 min.

The conjugate attached to CPG was added to 2 mL conc. ammonium hydroxide for 4 h. The solution was filtered and the filtrate was evaporated to afford crude sapphyrin-oligonucleotide conjugate which could be purified by fplc on a $C_{18}$ column using acetonitrile/100 mM triethylammonium acetate pH 7.0.

This method may be used to synthesize any type or length of oligonucleotide with macrocycle modifications at the 5' end or in the interior of the oligonucleotide. Additionally, the oligonucleotide could be modified with multiple macrocycles.

A further method for the synthesis of macrocycleoligonucleotide conjugates is to incorporate nucleotides enzymatically. A variety of DNA and RNA polymerases may be used, however, the Klenow fragment of DNA polymerase I from E. coli and terminal deoxynucleotidyl transferase are preferred. Goodchild, J. (Bioconjugate Chemistry., 1:165–187, 1990) provides a general discussion of the enzymatic synthesis of oligonucleotides and is incorporated by reference herein.

EXAMPLE 7

SELECTIVE DICARBOXYLATE TRANSPORT BY SAPPHYRIN DIMERS

To illustrate the binding of dicarboxylate anions by sapphyrin dimers, transport studies were carried out utilizing a standard U-tube model membrane system. Transport experiments were performed using a glass U-tube at 24°–26° C. Conditions: Source phase: 1 mL of a 1:1:1 ratio of 4-nitrophthalic acid, 5-nitroisophthalic acid and nitroterephthalic acid (10 mM of each) at pH 7.2 (adjusted by the addition of NaOH). Membrane (6 mL); carrier (1a or 23): 0.1 mM in dichloromethane. Receiving phase: 1 mL of $H_2O$, pH 7.0. The release of the dicarboxylate dianions into the receiving phase was monitored as a function of time via HPLC product analysis achieved using adenosine or uridine as the internal standards. In all cases, control experiments were performed in the absence of carrier. Error is within ±10%.

It was found that at neutral pH, dimer 23 acts as an efficient carrier for a range of dicarboxylates, including various isomers of nitrobenzene (Table 3). Further, in direct competition experiments (made using 23), nitroterephthalate dianion was found to be transported three times faster than 4-nitrophthalate dianion, suggesting a level of anion-based selectivity. On the other hand, none of the isomeric nitrophthalates was found to be transported effectively by the alkyl-substituted monomeric sapphyrin 1a.

TABLE 3

INITIAL RATES OF NITROBENZENE DICARBOXYLATE DIANION TRANSPORT

| Carrier[a,b] | $k_T$ ($10^{-10}$ mol/cm² · h) | | |
|---|---|---|---|
| | ortho | meta | para |
| 1a | 0.962 | 0.705 | 0.825 |
| 23 | 2.190 | 2.926 | 6.803 |

[a]0.1 mM in dichloromethane.
[b]Aq (I): 10 mM in each of 4-nitrophthalic acid, 5-nitroisophthalic acid and nitroterephthalic acid at pH 7.2 (adjusted by NaOH); Aq (II): pH 7.

EXAMPLE 8

DICARBOXYLATE BINDING EFFICACY WITH A SAPPHYRIN DIMER

Quantitative assessments of dicarboxylate binding efficacy in methanol were made using standard spectroscopic techniques. In general, $^1H$ NMR methods were employed, with the observed changes in the $^1H$ NMR chemical shifts of the aromatic protons of the carboxyl-containing substrate (kept constant in the mM concentration range) being monitored as a function of increased receptor concentration. In some instances, well-resolved shifts could not be observed in the appropriate $^1H$ NMR spectra. Here, either visible spectroscopic titration procedures were used or deuterated substrates were employed such that the binding process could be followed by $^2H$ NMR.

More specifically, binding studies were effected by means of $^1H$ NMR (General Electric QE-300), $^2H$ NMR (Bruker AM-500) and Vis (Beckman DU 640) titrations and were carried out at 293 K. using methanol as the solvent. Methanol-$d_4$ was used for the $^1H$NMR titrations and non-deuterated methanol was used for the $^2H$ NMR analyses. For both sets of NMR titrations, the substrate concentration was held constant and the receptor concentration varied. The change in the chemical shifts of the aromatic hydrogen/deuterium atoms of the substrates were then followed and used as a way of monitoring, in a relative way, the concentration of the bound and unbound species. For the Vis titrations, the receptor concentration was held constant and the substrate concentration varied. There, the change in absorption of the Soret-like band of receptor 23 was followed. Receptor 23 was used in the form of its bis-HCl salt, 23-2HCl. This salt was prepared by washing a dichloromethane solution of 23 (in its free-base form) three times with independent portions of an aqueous pH 6 solution of HCl, followed by 1) drying over $Na_2SO_4$, 2) evaporative removal of solvent and 3) drying in vacuo. Substrates were used as their trimethylammonium salts. They were prepared by dissolving the relevant dicarboxylic acid in methanol and then bubbling with trimethylamine gas for 10 min. The mixtures that resulted were evaporated to dryness on the rotor evaporator and then further dried under high vacuum. Terephthalic acid-$d_4$ was purchased from Aldrich Chemical Co. Isophthalic acid-$d_3$ was prepared according to a modification of a literature procedure: Lockley, W. J. S. J. Label. Comp. Radiopharm., 1984, 21, 45–57. Results are given in Table 4.

TABLE 4

BINDING CONSTANTS FOR COMPLEX FORMATION BETWEEN RECEPTOR 23 AND VARIOUS DICARBOXYLATE SUBSTRATES (S) IN METHANOL AT 293 K[a]

| S | $K_a(M^{-1})$[b] | Selectivity[c] |
|---|---|---|
| Phthalate | $K_1 = 310$[d]; $K_2 = 280$[d] | 1.2 |
| Isophthalate | 2 400[e], 2 500[f] | 9.4 |
| 5-Nitroisophthalate | 5 300[f] | 20.4 |
| Terephthalate | 4 600[e] | 17.7 |
| Nitroterephthalate | 9 100[f] | 35.0 |
| Benzoate | $K_1, K_2 = 1\ 380$[d] | 5.6 |
| | $K_1, K_2 = 1\ 530$[e] | |
| Oxalate | 260[f] | 1 |
| Malonate | 450[f] | 1.7 |

[a]Sapphyrin dimer 23 was used as its bis HCl salt, 23-2HCl. Substrates (S) were used as their $(CH_3)_3N$ H salts in order to prevent proton transfer to 23. Values of $K_a$ in selected cases were measured by two, or more methods with complete internal agreement being found.
[b]Complexes of 1:1 stoichiometry ($K_a$–$K_1$) were formed unless otherwise noted.
[c]Relative to the worst bound substrate, oxalate.
[d]Determined by $^1H$ NMR by titrating with receptor 23 while the concentration of the studied carboxylate ion was held constant at a value of 1–5 mM, depending on the measurement.
[e]Determined by $^2H$ NMR by titrating with receptor 23 while keeping the concentration of the carboxylate anion constant at a value of 1–5 mM, depending on the measurement.
[f]Determined by Vis spectroscopy by titrating in increasing amounts of the studied carboxylate anions (from $1 \times 10^{-6}$ to $1 \times 10^{-3}$M) into a solution of receptor 23 (initial concentration between $1 \times 10^{-6}$ and $5 \times 10^{-6}$M).

The results in Examples 7 and 8 show that sapphyrin dimers can be both an excellent and an inherently selective receptor for dicarboxylate anions. Sapphyrin dimer 23, for instance, shows little affinity for monocarboxylate-derived substrates while showing very good affinities for certain dicarboxylates. Interestingly, dimer 23 also displays a preference for linear over bent substrates and aromatic over aliphatic substrates that is remarkable given the inherently floppy nature of this receptor.

EXAMPLE 9

SAPPHYRIN MULTIMERS AS THERAPEUTIC AGENTS

The discoveries embodied by the present invention may be advantageously exploited in further scientific research, and importantly, in the development of new methods and compositions for treating various human diseases including cancer. Sapphyrins and their multimers are envisioned to be of use in a wide variety of clinical embodiments, including the binding, delivery and cellular transport of nucleotide derivatives, such as antiviral agents and dicarboxylates. The sapphyrin-sugar derivatives have the added potential of more specific cellular targeting according to sugar recognition by specific receptors. Sapphyrins and multimeric sapphyrins also have potential for use directly as chemotherapeutics.

Sapphyrin multimers also be used as a delivery agent for the intracellular targeting of any drug that has a phosphate group. Of course, given the synthetic methodology disclosed herein, it is contemplated that the sapphyrin multimers may be derivatized by the introduction of further groups to the periphery of the macrocycles, which groups would add the specificity and/or selectivity of the sapphyrin multimer-drug interaction. Sapphyrin multimer-drug interactions of this sort may be based upon either non-covalent interactions, or alternatively, may employ a covalent bond that is cleaved on exposure to the intracellular environment.

In particular embodiments, oligomers or polymers of sapphyrin or sapphyrin-nucleobase conjugates are envisioned to be of use in antisense technology. Such polymers will be of use both in the delivery and transport of oligonucleotides, and in enhancing their effectiveness once inside the target cell. The enhancing effect is based upon the properties of sapphyrin in binding to the phosphate portions of nucleic acids. This property will increase the affinity of the antisense construct for its target, and reduce diffusion which generally limits the effectiveness of an antisense molecule. This dual transport and binding role of sapphyrin-oligonucleotide conjugates in antisense treatments is particularly advantageous in that no other method or combination of methods available have a DNA (or RNA) affinity component.

The interaction between sapphyrin multimers and DNA, in which sapphyrin acts as a chelate for the phosphate backbone of DNA, is particularly important. The binding constant of unmodified sapphyrin for DNA has been determined to be on the order of $10^6 M^{-1}$, and evidence shows that the mode of DNA binding is not intercalation or groove binding. The inventors will extend these findings and construct, using all the available experimental evidence, computer models of the sapphyrin-DNA interaction. These models will allow the design and engineering of covalently linked multimeric sapphyrin molecules with increased affinity and specificity.

These second generation multimeric sapphyrin-based constructs should have a DNA affinity high enough to interfere with biological processes such as transcription and translation. It is contemplated that this will ultimately lead to the development of sapphyrin-based therapeutic agents for use in treating a variety of human diseases, including cancer.

Sapphyrin multimers themselves are also contemplated for use directly as chemotherapeutic agents. Currently available chemotherapeutics generally have complex structures, or complicated modes of interaction with their targets, that preclude systematic improvement. The development of a novel class of DNA binding compounds, namely the sapphyrin multimers of the present invention, therefore provides important opportunities for the development and use of novel therapeutic agents.

Due to the unique mode of sapphyrin-DNA interaction, the sapphyrin multimer possesses an unrivaled ability to act as a general DNA binding platform. Binding can also be modified so as to adjust both target cell specificity and degree of interaction with the DNA. For sapphyrins, importantly, the basic site of interaction with the DNA involves the interior of the sapphyrin macrocycle, so that the exterior positions $R^1$–$R^{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrins including alkylating functions (bromoacetamido groups, epoxides etc.) to provide covalent attachment to DNA or ene-diyne moieties to allow for double stranded DNA cleavage.

Sapphyrin multimers that bind to DNA simultaneously strengthen the entire interaction. This feature allows a modular approach in which the appropriate number (2–10) of sapphyrin molecules is attached in a single molecule, perhaps with different sapphyrin units containing sapphyrin derivatives with different groups attached that control such important properties such as solubility, target cell specificity and DNA modification ability.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Sessler, J. L.; Burrel, A. K. *Topics in Current Chemistry*, 1991, 161, 177–273.
2. V. J. Bauer, D. L. J. Clive, D. Dolphin, J. B. Paine, III, F. L. Harris, M. M. King, J. Loder, S. -W. C. Wang, R. B. Woodward, *J. Am. Chem. Soc.* 105 1983 6429–6436.
3. M. J. Broadhurst, R. Grigg, A. W. Johnson, *J. Chem. Soc., Perkin Trans.* 1 1972, 2111–2116.
4. (a) J. L. Sessler, M. J. Cyr, V. Lynch, E. McGhee, J. A. Ibers, *J. Am. Chem. Soc.*, 112 1990 2810–2813. (b) M. Shionoya, H. Furuta, V. Lynch, A. Harriman, J. L. Sessler, *J. Am. Chem. Soc.* 114 1992, 5714–5722.
5. H. Furuta, M. J. Cyr, J. L. Sessler, J. L. *J. Am. Chem. Soc.* 113 1991 6677–6678.

6. J. L. Sessler, M. J. Cyr, A. K. Burell, *Synlett.* 1991 127–133.
7. Robins, R. K. *Chemical and Engineering News* Jan. 27, 1986, 28–40.
8. *"Approaches to Antiviral Agents,"* Harden, M. R., Ed.; VCH Publishers: Deerfield Beach, Fla., 1985.
9. Holy, A. in *Approaches to Antiviral Agents,* Harden, M. R. (Ed.), VCH Publishers, Deerfield Beach, Fla., 1985, pp. 101–134.
10. (a) Tabushi, I.; Kobuke, Y.; Imuta, J. *J. Am. Chem. Soc.* 1981, 103, 6152–6157. (b) Kimura, E. *Top. Curr. Chem.* 1985, 128, 113–141. (c) Schmidtchen, F. P. *Top. Curt. Chem.* 1986, 132, 101–133. (d) Lehn, J.-M. *Angew. Chem., Int. Ed. Engl.,* 1988, 27, 89–112. (e) Marecek, J. F.; Fischer, P. A.; Burrows, C. J. *Tetradhedron Lett.* 1988, 29, 6231–6234. (f) Schmidtchen, F. P. *Tetrahedron Lett.* 1989, 30, 4493–4496. (g) Mertes, M. P.; Mertes, K. B. *Acc. Chem. Res.* 1990, 23, 413–418. (h) Hosseini, W.; Blacker, A. J.; Lehn, J.-M. *J. Am. Chem. Soc.* 1990, 112, 3896–3904. (i) Kimura, E.; Kuramoto, Y.; Koike, T.; Fujioka, H.; Kodama, M. J. *Org. Chem.* 1990, 55, 42–46. (j) Aoyama, J.; Nonaka, S.; Motomura, T.; Toi, H.; Ogoshi, H. *Chem. Lett.* 1991, 241–1244. (k) Claude, S.; Lehn, J.-M; Schmidt, F.; Vigneron, J. - P., *J. Chem. Soc., Chem. Commun.* 1991, 182–1185. (l) Deslongchamps, G.; Galán, A.; de Mendoza, J.; Rebek, J., Jr. *Agnew. Chem., Int. Ed. Engl.* 1992, 31, 61–63. (m) Dixon, R. P.; Geib, S. J.; Hamilton, A.D. *J. Am. Chem. Soc.* 1992, 114, 365–366. (n) Ariga, K.; Anslyn, E. V. *J. Org. Chem.* 1992, 57, 17–419. (o) Meuhldorf, A. V.; Van Engen, D.; Warner, J. C.; Hamilton, A.D. *J. Am. Chem. Soc.* 1988, 110, 561–6562. (p) Adrian, J. C.; Wilcox, C. S. *J. Am. Soc.* 1989, 111, 8055–8057. (q) Benzing, T.; Tjivikua, T.; Wolfe, J.; Rebek, J., Jr. *Science,* 1988, 242, 26668. (r) Seel, C.; Vögtle, F. *Angew. Chem. Int. Ed. Engl.* 1991, 30, 442–444. (s) Goodman, M. S.; Rose, S. D. *J. Am. Chem. Soc.* 1991, 113, 9380–9382. (t) Lindsey, J. S.; Kearney, P. C.; Duff, R. J.; Tjivikua, T.; Rebek, J. Jr. *J. Am. Chem. Soc.* 1988, 110, 6575–6577. (u) Ogoshi, H.; Hatekeyama, H.; Kotani, J.; Kawashima, A.; Kuroda, Y. *J. Am. Chem. Soc* 1991, 113, 8181–8183.
11. A. K. Burrell, J. L. Sessler, M. J. Cyr, E. McGhee, J. A. Ibers, *Angew. Chem.* 103 1991 83–85; *Angew. Chem. Int. Ed. Engl.* 30 (1991) 91–93.
12. J. L. Sessler, D. Ford, M. J. Cyr, H. Furuta, *J. Chem. Soc., Chem. Commun.* 1991, 1733–1735.
13. *The Biochemistry of the Nucleic Acids,* 10th ed., Adams, R. L. P.; Knowler, J. T.; Leader, D. P. (Eds.), Chapman and Hall, New York, 1986.
14. Furuta, H.; Furuta, K.; Sessler, J. L. *J. Am. Chem. Soc.* 1991, 113, 4706–4707.
15. Cell Surface Carbohydrate Chemistry, Ed. R. E. Harmon, Academic Press, N.Y., 1978, p. 225, G. A. Jarnieson: Surface Glycoproteins of Normal and Abnormal Platelets p. 311: B. Paul, W. Korytnyk: Cell Surface as a target for chemotherapy. Potential inhibitors of Biosynthesis of Protein-Carbohydrate Linkage in Glycoproteins.
16. R. J. Bernacki, M. Sharma, N. K, Poter, Y. Rustum, B. Paul, W, Korytnyk: *J. Supramol. Structure* 7, 235–250 1977.
17. Sessler, J. L.; Morishima, T.; Lynch, V. *Angew. Chem., Int. Ed. Eng.* 1991, 30, 977–980.
18. Furuta, H.; Morishima, T.; Král, V.; Sessler, J. L., *Supramolec. Chem.,* in press.
19. Sessler, J. L.; Magda, D.; Furuta, H. *J. Org. Chem.* 1992, 57, 818–826.
20. Tsukube, H. in *Liquid Membranes: Chemical Applications,* Araki, T.; Tsukube, H. (Eds.), CRC Press, Boca Raton, 1990, pp. 27–50.
21. Phillips, R.; Eisenberg, P.; George, P.; Rutman, R. J. *J. Biol. Chem.* 1965, 240, 4393–4397.

What is claimed is:

1. A sapphyrin multimer having structure I:

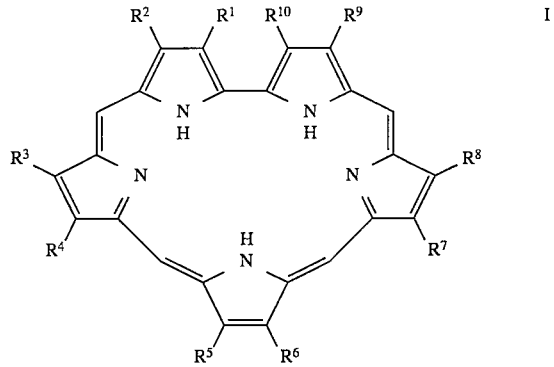

wherein each of $R^1$—$R^{10}$ are independently hydrogen, alkyl, alkene, alkyne, halide, alkylhalide, hydroxyalkyl, hydroxyalkylamido, glycol, polyglycol, thiol, thioalkyl, aminoalkyl, carboxyalkyl, carboxyamidealkyl, oxyalkyl, alkoxyalkyl, aryloxyalkyl, oxyhydroxyalkyl, alkyloxycarbonyl, aryloxycarbonyl, aldehyde, ether, ketone, carboxylic acid, phosphate, phosphonate, saccharide, nucleobase, sulfate, phosphate substituted alkyl, phosphonate substituted alkyl or sulfate substituted alkyl; wherein at least one of $R^1$-$R^{10}$ is of the formula $(CH_2)_n$—A—$(CH_2)_m$—B, where A is alkyl, oxy, sulfide, amide, carbonyl, alkenyl, alkynyl, aryl, alkylhalide, hydroxyalkyl, glycol, polyglycol, alkylthiol, substituted alkyl, phosphate, phosphonate, sulfate, phosphate substituted alkyl, phosphonate substituted alkyl, sulfate substituted alkyl, carbonate, carbamate, bis(aminoguanidinium), carboxy, carboxyamide, carboxyamidealkyl, carboxyamidearyl, thiol-substituted carboxyamide, or derivatized carboxyamide;

B is a sapphyrin, or a sapphyrin derivative, or an oligomer or polymer of sapphyrin or of a sapphyrin derivative having up to about 200 sapphyrin units; and n and m are independently an integer from 0 to 10.

2. The sapphyrin multimer of claim 1 wherein A is carboxyamidearyl; B is a sapphyrin or a sapphyrin derivative; and n and m are independently 1, 2 or 3.

3. The sapphyrin multimer of claim 1 wherein A is carboxyamidealkyl; B is a sapphyrin or a sapphyrin derivative; and n and m are independently 1, 2 or 3.

4. The sapphyrin multimer of claim 3 wherein B is a sapphyrin derivative and the sapphyrin derivative is hydroxyalkyl, saccharide or aminosaccharide derivative.

5. The sapphyrin multimer of claim 1 wherein A is carboxyamidealkyl bound to a further amide; and the further amide is covalently bound to two molecules of B to form a tethered sapphyrin trimer.

6. The sapphyrin multimer of claim 1 wherein B is a sapphyrin or sapphyrin derivative and B is further bound to a third sapphyrin or sapphyrin derivative to form a linear sapphyrin trimer.

7. The sapphyrin multimer of claim 6 wherein the linear sapphyrin trimer is covalently bound to form a cyclic trimer.

8. The sapphyrin multimer of claim 1 wherein A is carboxyamidealkyl bound to a further amide; the further amide being covalently bound to a second sapphyrin and a linker, the linker being bound to a third and a fourth sapphyrin to form a tethered sapphyrin tetramer.

9. The sapphyrin multimer of claim 8 wherein the linker is a tertiary amine.

10. The sapphyrin multimer of claim 1 wherein B is an oligomer or polymer of sapphyrin or sapphyrin derivative.

11. The sapphyrin multimer of claim 10 where B is a polymer of sapphyrin or sapphyrin derivative having from 4 to about 200 sapphyrin units.

12. The sapphyrin multimer of claim 9 wherein A is phosphate.

13. The sapphyrin multimer of claim t wherein at least one of $R^1$–$R^{10}$ is a nucleobase.

14. The sapphyrin multimer of claim 13 where B is a sapphyrin derivative and the derivative is a nucleobase.

15. The sapphyrin multimer of claim 11 wherein B is a polymer of sapphyrin derivative and the derivative is a nucleobase.

16. The sapphyrin multimer of claim 15 further comprising a noncovalently bound oligonucleotide.

17. A sapphyrin multimer having structure 14, 15, 15b, 15c, 19, 21, 22, 23, 24, 25, 26, 27, 34, 35, or 36.

18. A method of making a sapphyrin multimer comprising the steps of obtaining a sapphyrin or sapphyrin derivative, and reacting the sapphyrin or sapphyrin derivative with a further sapphyrin or sapphyrin derivative to form a sapphyrin multimer.

19. A method of binding an anion comprising the step of contacting the anion with a multimeric sapphyrin or sapphyrin derivative.

20. The method of claim 19 where the anion is a phosphate anion or a dicarboxylate anion.

* * * * *

UNITED STATES PATENT AND TRADEMARK OFFICE
CERTIFICATE OF CORRECTION

PATENT NO.    :   5,587,478

DATED         :   December 24, 1996

INVENTOR(S)   :   Sessler et al.

It is certified that error appears in the above-identified patent and that said Letters Patent is hereby corrected as shown below:

In claim 13, column 57, line 8, please delete "claim t" and insert -- claim 1 -- therefor.

Signed and Sealed this

Twenty-fifth Day of March, 1997

*Attest:*

BRUCE LEHMAN

*Attesting Officer*   *Commissioner of Patents and Trademarks*